US006368794B1

(12) United States Patent
Daniel et al.

(10) Patent No.: US 6,368,794 B1
(45) Date of Patent: Apr. 9, 2002

(54) DETECTION OF ALTERED EXPRESSION OF GENES REGULATING CELL PROLIFERATION

(75) Inventors: Steven Daniel, Gilroy; James Gilmore, San Jose; Susan G. Stuart, Montara; Laura L. Stuve, Los Gatos, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/232,160

(22) Filed: Jan. 15, 1999

(51) Int. Cl.[7] .................. C12Q 1/68; C07H 21/04; C07H 21/02
(52) U.S. Cl. ................ 435/6; 536/22.1; 536/23.1; 536/24.5
(58) Field of Search .............. 435/6; 536/22.1, 536/23.1, 24.5

(56) References Cited

U.S. PATENT DOCUMENTS 5,739,009 A * 4/1998 Hillman et al. ............ 435/69.1

OTHER PUBLICATIONS

Nishiu et al., "Isolation and Chromosomal Mapping of the Human Homolog of Perilipin (PLIN), a rat Adipose Tissue–specific Gene, by Differential Display Method", *Genomics*, vol. 48, pp. 254–257, Feb. 1998.*

Madisen et al., "Molecular cloning of a Novel Bone–Forming Compound: Osteoinductive Factror", *DNA and Cell Biology*, vol. 1, No. 5, pp. 303–309, May 1990.*

Derisi et al., "Use of cDNA microarray to analyse gene expression patterns in human cancer", Nature Genetics, vol. 14, pp. 457–460, Dec. 1996.*

Sugita et al., "Genebank Accession No.: AB000111", Dec. 1996.*

Madisen et al., "Molecular cloning of a novel bone–forming compound: osteoinductive factor", DNA and Cell Biology, vol. 9(5), pp. 303–309, Sep. 1990.*

Nguyen, C., et al, Differential Gene Expression in the Murine Thymus Assayed by Quantitative Hybridization of Arrayed cDNA Clones, *Genomics* 29:207–216, (1995).

Velculescu, V.E., et al, Serial Analysis of Gene Expression, *Science*, 270:484–487, (1995).

Liang, P., et al, Differential Display of Eukaryotic Messenger RNA by Means of the Polymerase Chain Reaction, *Science*, 257:967–971, (1992).

Prashar, Y., et al, Analysis of differential gene expression by display of 3' end restriction fragments of cDNAs, *Proc. Natl Acad Sci*, 93:659–663, (1996).

Rao, VB, Abstract, Direct sequencing of polymerase chain reaction–amplified DNA, *Anal Biochem*, 216(1):1–14, (1994).

Madisen, L., et al. (Direct Submission), GenBank Sequence Database (Accession AAA30670), National Center for Biotechnology Information, National Library of Medicine, Bethesda, Maryland, 20894 (G163430), Jan. 11, 1991.

Zhou, D., et al, (Direct Submission), GenBank Sequence Database (Accession AAC13419), National Center for Biotechnology Information, National Library of Medicine, Bethesda, Maryland, 20894 (G3046386), Sep. 15, 1998.

Yu, W., et al, (Direct Submission), GenBank Sequence Database (Accession AF035283), National Center for Biotechnology Information, National Library of Medicine, Bethesda, Maryland, 20894 (G2661034) Dec. 04, 1997.

Kimmel, A.R., et al, (Direct Submission), GenBank Sequence Database (Accession AAA41830), National Center for Biotechnology Information National Library of Medicine, Bethesda, Maryland, 20894 (G457374), Mar. 01, 1994.

* cited by examiner

Primary Examiner—Jeffrey Fredman
Assistant Examiner—Arun K. Chakrabarti
(74) Attorney, Agent, or Firm—Incyte Genomics, Inc.

(57) ABSTRACT

The present invention relates to polynucleotides comprising genes that regulate cell proliferation. The present invention also relates to a method for diagnosing or monitoring the treatment of a disease characterized by the altered expression of genes that regulate cell proliferation in a sample.

9 Claims, No Drawings

SEQUENCE LISTING

<160> NUMBER OF SEQ ID NOS: 23

<210> SEQ ID NO 1
<211> LENGTH: 2728
<212> TYPE: DNA
<213> ORGANISM: Homo sapiens
<220> FEATURE: -
<223> OTHER INFORMATION: 159452

<400> SEQUENCE: 1
cgagacatag cttttctcat tcaccctcac acttggggct aatgcacaga catgaacatc      60

```
tattgaggaa aaccacaaaa aacttcaaaa cagctacaac gggaaaaaga gagttttgtc      120
ccacagtcag caggccacta gtttattaac ttccagtcac cttgattttt gctaaaatga      180
agactctgca gtctacactt ctcctgttac tgcttgtgcc tctgataaag ccagcaccac      240
caacccagca ggactcacgc attatctatg attatggaac agataatttt gaagaatcca      300
tatttagcca agattatgag gataaatacc tggatgaaaa aaatattaag gaaaaagaaa      360
ctgtgataat acccaatgag aaaagtcttc aattacaaaa agatgaggca ataacaccat      420
tacctcccaa gaaagaaaat gatgaaatgc ccacgtgtct gctgtgtgtt tgtttaagtg      480
gctctgtata ctgtgaagaa gttgacattg atgctgtacc acccttacca aaggaatcag      540
cctatcttta cgcacgattc aacaaaatta aaaagctgac tgccaaagat tttgcagaca      600
tacctaactt aagaagactc gattttacag gaaatttgat agaagatata aagatggta       660 cttttttcaaa actttctctg ttagaagaac tttcacttgc tgaaaatcaa ctactaaaac      720
ttccagttct tcctcccaag ctcacttttat ttaatgcaaa atacaacaaa atcaagagta      780
ggggaatcaa agcaaatgca ttcaaaaaac tgaataacct caccttcctc tacttggacc      840
ataatgccct ggaatccgtg cctcttaatt taccagaaag tctacgtgta attcatcttc      900
agttcaacaa catagcttca attacagatg acacattctg caaggctaat gacaccagtt      960
acatccggga ccgcattgaa gagatacgcc tggagggcaa tccaatcgtc ctgggaaagc     1020
atccaaacag ttttatttgc ttaaaaagat taccgatagg gtcatacttt taacctctat     1080
tggtacaaca tataaatgaa agtacaccta cactaatagt ctgtctcaac aatgagtaaa     1140
ggaacttaag tattggttta atattaacct tgtatctcat tttgaaggaa tttaatattt     1200
taagcaagga tgttcaaaat cttacatata ataagtaaaa agtaagactg aatgtctacg     1260
ttcgaaacaa agtaatatga aaatatttaa acagcattac aaaatcctag tttatactag     1320
actaccattt aaaaatcatg ttttatata aatgcccaaa tttgagatgc attattccta      1380
ttactaatga tgtaagtacg aggataaatc caagaaactt tcaactcttt gcctttcctg     1440
gcctttactg gatcccaaaa gcatttaagg tacatgttcc aaaaactttg aaaagctaaa     1500
tgtttcccat gatcgctcat tcttctttta tgattcatac gttattcctt ataaagtaag     1560
aactttgttt tcctcctatc aaggcagcta ttttattaaa ttttcactt agtctgagaa      1620 atagcagata gtctcatatt taggaaaact ttccaaataa aataaatgtt attctctgat     1680
aaagagctaa tacagaaatg ttcaagttat tttactttct ggtaatgtct tcagtaaaat     1740 attttctttta tctaaatatt aacattctaa gtctaccaaa aaaagtttta aactcaagca     1800
ggccaaaacc aatatgctta taagaaataa tgaaaagttc atccatttct gataaagttc     1860
tctatggcaa agtctttcaa atacgagata actgcaaaat attttccttt tatactacag     1920
aaatgagaat ctcatcaata aattagttca agcataagat gaaaacagaa tattctgtgg     1980
tgccagtgca cactaccttc ccacccatac acatccatgt tcactgtaac aaactgaata     2040
ttcacaataa agcttctgag taacactttc tgattactca tgataaactg acatggctaa     2100
ctgcaagaat taaatcttct atctgagagt aataatttat gatgactcag tggtgccaga     2160
gtaaagtttc taaataaca ttcctctcac ttgtacccca ctaaaagtat tagtctacac      2220 attcattga agttaaacac aaaattatca gtgttttaga aacatgagtc cggactgtgt      2280
aagtaaaagt acaaacatta tttccaccat aaagtatgta ttgaaatcaa gttgtctctg     2340
tgtacagaat acatacttat tcccattttt aagcatttgc ttctgttttc cctacctaga     2400
```

-continued

| | |
|---|---|
| atgtcagatg ttttttcagtt atctccccat ttgtcaaagt tgacctcaag ataacatttt | 2460 |
| tcattaaagc atctgagatc taagaacaca attattattc taacaatgat tattagctca | 2520 |
| ttcacttatt ttgataacta atgatcacag ctattatact actttctcgt tattttgtgt | 2580 |
| gcatgcctca tttccctgac ttaaacctca ctgagagcgc aaaatgcagc tttatacttt | 2640 |
| ttactttcaa ttgcctagca caatagtgag tacatttgaa ttgaatatat aataaatatt | 2700 |
| gcaaaataaa atccatctaa ataaaaaa | 2728 |

<210> SEQ ID NO 2
<211> LENGTH: 2125
<212> TYPE: DNA
<213> ORGANISM: Homo sapiens
<220> FEATURE:
<221> NAME/KEY: unsure
<222> LOCATION: 52
<223> OTHER INFORMATION: a or g or c or t, unknown, or other
<220> FEATURE: -
<223> OTHER INFORMATION: 914930

<400> SEQUENCE: 2

| | |
|---|---|
| ccccccaaac ggaaggaagc ccccatgccc ccaaaagcag ccaaacctat tnttggttta | 60 |
| tttaatggtg tagcttttta actttattaa agaatttacc agcgaaaccc ttacatgagt | 120 |
| aattgaaatg aaattaaatg agattacagc ataatgaaga agaaaactag aatctaacag | 180 |
| gtatgacaca ttcagttatt ctaacagggc acagtactgt gctatatgta gccgcccttta | 240 |
| cagatgttat taacctatag tagtttacta ttaactagga agactggtgt atgaggaggg | 300 |
| agacattctg taataagatt aaaacctaaa gtcagctgtg taacattcca tgaaagatgc | 360 |
| attcatttat tgaagatgac aaaaaaggga gtcagatata ttctggaagc tattttaatt | 420 |
| ttaggcacac aatctcatac attttgagac ccttgggtca tttattactt tttacaaact | 480 |
| agttcctctc ttttttttctg ccaagtcctg aattgaaaac tgtaggcttc cttgcacaga | 540 |
| tgttgcagcc agcctcagga gtaaagtgcc cgctgactgc tgccgccacc tctgtctcgc | 600 |
| tccctgtcag tgctgctggc acgtgggacg cggcaggtga cagccgttct cagcatgttt | 660 |
| tagaagcttg cctcacagac ttccatgcct ctccattcag ccgatgactt caaggtgtca | 720 |
| aactgttttta attttttcaaa caaatggaac agaagccatt gtggttcatc ctgattactt | 780 |
| gaacgttgca cttggtggac cgtgcctggg agcgctcgca tgcccctgg cttcagaagt | 840 |
| catgtcagtg tctctgtaga caaactccac tgtacatctt ggattaatct tctgattcat | 900 |
| tgttcatttt ctcaagactt tttgtggaat tctctgataa aggaagcttt taggatggta | 960 |
| tctatcaggc caccagcagg aattgaaaat gttttcacaa aaatccttt ccttagaaat | 1020 |
| aaaagctggt gacagagatg gtttccttgt accgataaaa acaaaaccaa atccatatta | 1080 |
| tacatcaaaa ccttgtgaga cattcacttg ctcttttgcc atatttagat gtgttagtgg | 1140 |
| aatcagaaac ctgttttgat atgtgttctc catgagttaa gtctgatttg tcttttatt | 1200 |
| tcatgatgca tgtctttttt tttcttttgt caggataacg tcatatagca tcttgtttgt | 1260 |
| ttttccttat ctctatgtac atatctatct acttctgact gtagatgggt atatagatag | 1320 |
| atgccaagct tcttatgttc tggggtagt atgcatcatt attgggtctc tgccttaaaa | 1380 |
| cacatcaaaa ttcattttag acaaaaaaac ttctgctttg tctttggtca ttagggagct | 1440 |
| ctaatgtgtg tttgtggctc caagttacat tttgtgtttc attgatctat atgtatatat | 1500 |
| gtgatgtttt catatatata tgtgtgtgtg tttaaatttt gtatcatcag gactgacacc | 1560 |
| caatttgaca cttttttgtat ctagaagacc ctccaaaaaa ggaaccacat aagcacacaa | 1620 |

-continued

```
gaaaagagtg ctatgatgtt cttagcattt gctatcatgc ctatttttat ctagattttt      1680
aaatgtagct tgtcataaca aaattttaat tacaattggc ttgtatgaga agaaaaagta      1740 ttttattgt tttgagtgat gacgcagaga ctcaatgaac ttgaaaatag cattgcttcg       1800
tgcactttga ataccaatca ggtgttttct gtgctactag ttgtcacgtt gcattcatgt      1860
tcacctcctg atttaagtat ctcgggtgtg cccagccact aaagcactct ggactaatcg      1920
ctaaagagaa gcaacgtggg gggtggggtt gcgagggatg tgttcacatg tacccatcat      1980
ttgatcatag cactgtgatt gcttttgatg tgtgtctcta gtggtgtgtt gtctgttggc      2040
atgcttaaag cacatgtcca ttaaaattca ttttgttcct tttaaaaaaa aaaaaaaagg      2100
gcggccccga ctagtgagcc cgtcg                                            2125
```

<210> SEQ ID NO 3
<211> LENGTH: 1853
<212> TYPE: DNA
<213> ORGANISM: Homo sapiens
<220> FEATURE: -
<223> OTHER INFORMATION: 1283330

<400> SEQUENCE: 3

```
tgttttctcc cccatcacaa aaaaaaaat tcttatttt agtagacatg tatttaccaa          60
aaatatgtac tcaattattg tattttggat tttatcaatt taaaaattgt ggaaatttgt      120
ttgctcttac gccaacataa tattgatttt gcctcttggc tctgaaagcc caaatatttt     180
accgtctagc ccgttacaga aaagtctgc tgactactga gccagacctc cattacctcc      240
atccctgttg gattatttaa agaaagcctc agacagtaag ggctttttta aaagaataaa     300
atgacttggt ttgcgcttgg aagcagggga agcattcaga tgagcggttt ctgcattaac    360
cctgcctatc acgcatctcg tgtcctgtgt ggctggcgag ccccccttgg aaggttctgg    420
tgcttcagct ggctcctgca gagtccaccc cgcctcgtgg tgggaatgca gagcccttg     480 cttttccttct gccgcctgc ttcctgttcc tggggacccg ctgggccttt ggtctgcatc    540
ccctggccag gtccctcagg gttgatgcgt ggagaaggac tttgagcagt ggtgggcagc    600
agtggcctcc tggccagctc acactcttgt cctgggaggg gcagcctgat ctcacctcca    660
cctagtacct tggggactga ggaccttttg gcttctctgg agcctgcaag cctcttccca    720
tgtgtccagc tgctcttcct gctacaaagg ggactgctca cagtggcctc agcttggtgg    780
ttttgagggg ccgcccccg gccctccata agggtatcct gggcctgaga attctgcatc    840
tgccattgga ggatggacag cctcaaatgg aaggagtccc acgggagatg ggtccgaggt    900
ccggctgtgg ccatccagcc ccctgtggct tgtccagcct ctgtgcaccc ctggtgtctt    960
cactccaggg gcagacagca gccactgcag ttcctttctt cgtgagtaac agtagtgata   1020
gcagctgggg ctaacaggct aggctttgtg ttctgcgcat ttggtcagct tctcactcga   1080
tcctccctaa agcaatgggg aggccccac tagcccagtt tcaggaagt caactgggag    1140 gttagatggg ggcagggtc ccacagctac tgatggcccg agccaggttg agcttcctgg    1200
tgtccagtcc ggatcccact tgcagatctc atgctctcag ataggtggga caagttcttt   1260
tgtcacagtg ctggctctgt cctgaggcct cattgctggc tgggtgtgct ctgctgggaa   1320
aagctttgcg gggcttgctt ggttaaccac agaagagaag gggactgttt ggggtgcctc   1380
tctgcagcct cccgtgctg ggtggaagca cggttactgt gttctctaat gttcatgtat   1440
ttaaaatgat ttctttctaa agatgtaacc tccacacctt tctccagatt gggtgactct   1500
```

```
tttctaaagg tggtgggagt atctgtcggg gtggtgtggc ccttggatgg gtcaggtggg    1560
tgtgagaggt cctggggagg tgggcgttga gctcaaagtt gtcctactgc catgttttg     1620 tacctgaaat aaagcatatt ttgcacttgt tactgtacca tagtgcggac gagaagtctg    1680
tatgtgggat ctgtgcttgg gttagaatgc aaataaaact cacatttgta agacaaaaaa    1740
aaaaacaaaa gagagaccca gcccaaggag acatacagta aacgagggga gtaaaagagg    1800
tcgaagaaac tcgacaagag acgaagtaaa aaaggggcg gccccccct ttt             1853
```

<210> SEQ ID NO 4
<211> LENGTH: 1741
<212> TYPE: DNA
<213> ORGANISM: Homo sapiens
<220> FEATURE: -
<223> OTHER INFORMATION: 1299627

<400> SEQUENCE: 4

```
ttcgctccaa gcctcaggcc accggcttgg atggacgctc cgaggctacc cgtgcgtcca     60
ggggtcttgc ttccgaagtt ggtcctgctc tttgtctacg cagatgattg ccttgctcag    120
tgtggcaaag attgcaaatc ttactgctgt gatggaacca cgccctactg ttgctcctac    180
tacgcttata ttgggaatat cctctcgggc actgcaattg cgggcattgt ttttggaata    240
gtatttatca tgggggtcat tgctgggatt gccatatgca tctgcatgtg catgaagaac    300
cacagggcga cccgcgtggg catcctcagg acgactcaca tcaacaccgt ctcctcctat    360
cctggaccac caccctacgg tcacgaccac gagatggaat actgtgcaga cttgcctcct    420
ccatactccc ccaccccaca gggtccagca cagcgttctc cacccctcc ttatcctgga    480 aacgcaagga ataatctat ctcccagaac agaacatgtg ccaatgggcg atcttgcctg    540
gaataaaatg cctctactca gaaacaggca ggaaagaatt gctccaagga atacttttg    600 gggtcagata atgtgtcagg tggaatatcc ctgctaggag atataggatt tctactctgc    660
tcaaagctga ccccatctgg agtattaatg tttggttcta tggaaccaca ttttaagaga    720
tctgctgatc cacctaagca cattcaggga agagtaatgt aattgacaaa atatctgata    780
atcatgttgt ttaagggcta ggtgaagaaa gtttcagtat tgatcctgga aaaaagaag     840 atctaagtag gatgggagaa tgatttggcc cacacaagga agcaactta ttctatatag     900 ctttaaaagt cagaactaga attgttcatt cttcatca tcaataaatg tatttgagt     960 gcctaagagt ttactatgtg cctagcactg tttgaggtcc tgatggaagt tacaggatgg    1020
gtactctggt tttagtacaa gaaagagcaa tgactagatt gctttgtgaa gctcttggta    1080
gagacacgct ccagaaggga taacaaaatc aaatagtaga tgggttcatt gggcctcaga    1140
agttctgctc gtattttagg tgggtgtgaa gtgaatttct atatgtccag gagtgaatac    1200
aacagaaaga gttggatctt atttatttaa ttagggagtt aaaacaagac caaaagact     1260 caacagccgc ttgaagccaa gaactcttca atgccagcta ctgccaccta aaaatcatct    1320
ggctttatag tggatcagaa taaggttat tctaactgtg gggagaaaaa aaaaattgta    1380
tcaagttcca caggtagcag acacttcact tccaagtaaa agatgagaaa tcaattattc    1440
ccacaggatt ttaggtcagg gagcaaaaat ctcagaactt gaccatgaag atacacaaca    1500
gactcgcaaa aataaagtgg gaaatgaagt tcagattccc ttctgtagat ttccttaaaa    1560
ctattatttt tttcttcttc gtaaaatttt gataatctgt tctcttaaaa aagttaatga    1620
cacaattaag atactgacat caaattgttg ccttttacca aaatgcaaat tttatgaagt    1680
gcctaccttt atatgtataa agcatttaat aaataattct aatgtgccat aaaaaaaaa     1740
``` a                                                                          1741

<210> SEQ ID NO 5
<211> LENGTH: 2678
<212> TYPE: DNA
<213> ORGANISM: Homo sapiens
<220> FEATURE: -
<223> OTHER INFORMATION: 1319129

<400> SEQUENCE: 5

| | | | | | |
|---|---|---|---|---|---|
| tcggaattcg | gctcgagata | gactgtgagt | tctgtggtga | cagaaaccaa | gtgtaacctg    60 |
| tttaccattt | gattcccagc | acctggcata | gtgcctgaaa | tgtactgttc | gggggtcttg   120 |
| tctggatttt | ggttgcctcc | tccaatgttc | ctctacctct | actacaagga | tgggtcatgt   180 |
| ttgtgtccgt | gacagcgttt | ttcttttcgc | tcctctttct | gggcatgttc | ctctctggca   240 |
| tggtggctca | aattgatgct | aactggaact | tcctggattt | tgcctaccat | tttacagtat   300 |
| ttgtcttcta | ttttggagcc | ttttattgg  | aagcagcagc | cacatccctg | catgatttgc   360 |
| attgcaatac | aaccataacc | gggcagccac | tcctgagtga | taaccagtat | aacataaacg   420 |
| tagcagcctc | aattttgcc  | tttatgacga | cagcttgtta | tggttgcagt | ttgggtctgg   480 |
| ctttacgaag | atggcgaccg | taacactcct | tagaaactgg | cagtcgtatg | ttagtttcac   540 |
| ttgtctactt | tatatgtctg | atcaatttgg | ataccatttt | gtccagatgc | aaaaacattc   600 |
| caaaagtaat | gtgtttagta | gagagagact | ctaagctcaa | gttctggttt | atttcatgga   660 |
| tggaatgtta | atttattat  | gatattaaag | aaatggcctt | ttatttaca  | tctctcccct   720 |
| ttttcccttt | cccccttat  | tttcctcctt | ttctttctga | aagtttcctt | ttatgtccat   780 |
| aaaatacaaa | tatattgttc | ataaaaaatt | agtatccctt | ttgtttggtt | gctgagtcac   840 |
| ctgaacctta | attttaattg | gtaattacag | cccctaaaaa | aaacacattt | caaataggct   900 |
| tcccactaaa | ctctatattt | tagtgtaaac | caggaattgg | cacacttttt | ttagaatggg   960 |
| ccagatggta | aatatttatg | cttcacggtc | catacagtct | ctgtcacaac | tattcagttc  1020 |
| tgctagtata | gcgtgaaagc | agctatacac | aatacagaaa | tgaatgagtg | tggttatgtt  1080 |
| ctaataaaac | ttatttataa | aaacaagggg | aggctgggtt | tagcctgtgg | gccatagttt  1140 |
| gtcaaccact | ggtgtaaaac | cttagttata | tatgatctgc | attttcttga | actgatcatt  1200 |
| gaaaacttat | aaacctaaca | gaaaagccac | ataatattta | gtgtcattat | gcaataatca  1260 |
| cattgccttt | gtgttaatag | tcaaatactt | acctttggag | aatacttacc | tttggaggaa  1320 |
| tgtataaaat | ttctcaggca | gagtcctgga | tataggaaaa | agtaatttat | gaagtaaact  1380 |
| tcagttgctt | aatcaaacta | atgatagtct | aacaactgag | caagatcctc | atctgagagt  1440 |
| gcttaaaatg | ggatccccag | agaccattaa | ccaatactgg | aactggtatc | tagctactga  1500 |
| tgtcttactt | tgagtttatt | tatgcttcag | aatacagttg | tttgccctgt | gcatgaatat  1560 |
| acccatattt | gtgtgtggat | atgtgaagct | tttccaaata | gagctctcag | aagaattaag  1620 |
| tttttacttc | taattatttt | gcattacttt | gagttaaatt | tgaatagagt | attaaatata  1680 |
| aagttgtaga | ttcttatgtg | tttttgtatt | agcccagaca | tctgtaatgt | ttttgcactg  1740 |
| gtgacagaca | aaatctgttt | taaaatcata | tccagcacaa | aaactatttc | tggctgaata  1800 |
| gcacagaaaa | gtattttaac | ctacctgtag | agatcctcgt | catggaaagg | tgccaaactg  1860 |
| ttttgaatgg | aaggacaagt | aagagtgagg | ccacagttcc | caccacacga | gggcttttgt  1920 |
| attgttctac | tttttcagtc | ctttactttc | tggctgaagc | atccccttgg | agtgccatgt  1980 |

-continued

| | |
|---|---|
| ataagttggg ctattagagt tcatggaaca tagaacaacc atgaatgagt ggcatgatcc | 2040 |
| gtgcttaatg atcaagtgtt acttatctaa taatcctcta gaaagaaccc tgttagatct | 2100 |
| tggtttgtga taaaaatata aagacagaag acatgaggaa aaacaaaagg tttgaggaaa | 2160 |
| tcaggcatat gactttatac ttaacatcag atcttttcta taatatccta ctactttggt | 2220 |
| tttcctagct ccataccaca cacctaaacc tgtattatga attacatatt acaaagtcat | 2280 |
| aaatgtgcca tatggatata cagtacattc tagttggaat cgtttactct gctagaattt | 2340 |
| aggtgtgaga ttttttgttt cccaggtata gcaggcttat gtttggtggc attaaattgg | 2400 |
| tttcttaaa atgctttggt ggcacttttg taaacagatt gcttctagat tgttacaaac | 2460 |
| caagcctaag acacatctgt gaatacttag atttgtagct taatcacatt ctagacttgt | 2520 |
| gagttgaatg acaaagcagt tgaacaaaaa ttatggcatt taagaattta acatgtctta | 2580 |
| gctgtaaaaa tgagaaagtg ttggttggtt ttaaaatctg gtaactccat gatgaaaaga | 2640 |
| aatttatttt atacgtgtta tgtctctaat aaagtata | 2678 |

<210> SEQ ID NO 6
<211> LENGTH: 1585
<212> TYPE: DNA
<213> ORGANISM: Homo sapiens
<220> FEATURE: -
<223> OTHER INFORMATION: 1698542

<400> SEQUENCE: 6

| | |
|---|---|
| tgggctcggg tgtggggcc ctagctcgcc ctctctgggt gggtgggtga gagaggctgc | 60 |
| agggaggct ggcaccgggc ttgggcctcc agtccctgcc ttgctgactt tggccgttgc | 120 |
| ggtatcacgt gacaatcaac tctcccttaa cgacgactgc ggctgttggg ctgcgctgcc | 180 |
| ctccctggcc tgcaggtggg gccgtggagc ccatgcccgc cggggttgca ggctcttccg | 240 |
| ggcctgggct gcagcctggc ccggccctgc ttccctggcc tccctccctt ctcctgggtg | 300 |
| cttggaagag gtgggtcctg gcccgtggtt gaggtcttgc ctcgtggact ggaagcagag | 360 |
| ggctggctgt gcagcctcct ggggtagctc gttttttttg caccgggtag aatatttttt | 420 |
| caggcacgga ttcctttttt tctgggcccc catgggtggt ccggcatcct caggggtgt | 480 |
| gagtgtgtgt gggggtctc tgagctgaac ttgggtgggg tggggacttg ttcctcgggg | 540 |
| gccacctttg tgtccttgtc agcggtcgtc ctgctgtggc ctgggttgca tttcctcttg | 600 |
| gggggggtat tgaggacccc cagcctggaa tgagaagggt ccccggttcc atgtcagacc | 660 |
| cagaaaggtg gatcccccca ctgttggctg caggaggttt ttggtacccc cttttgttcc | 720 |
| agaaccgtcc tgcctctcgc ttggggacag ggggctttg gatggcactg gtgtgcacct | 780 |
| ggacccagcc ccggcctggc aggatccagg gatgggtgcc tgggatcctg gggggaggga | 840 |
| ggcagggac gcccttctgg agctgggctc ggagggtcct gccccatcca gccctcggct | 900 |
| ctctgtgttc tctgtcccta gcctcaaacc ctcttctggc agcgctagtg agatgcctta | 960 |
| gtctgtgggg gtgggtgggg gactgggcc ccgttttcct ttgtgagtct tggttggccc | 1020 |
| cagccctggc aggggcctgt ctggagcagg ggtaggtagg gctgtgggtt ccagaactct | 1080 |
| ataactgggc ccctctccag tgtccagggg cttggagaga cctgcgccca ccctccact | 1140 |
| ctcccaggag tcgctgatca ctgggacctg gttccagccg tttgcagggg aggcggctcc | 1200 |
| gagaggcgtg tgctttccgt gggtggcgc cctcccccgc cctgcctggc ctcatccttg | 1260 |
| tatttaatta attaaacaag cccctttta aaccctaaaa aaaaaggca gaagcaacat | 1320 |
| aacaaacagg aaacctataa gaaagaggaa gcacgtgaga aaaaaaaaaa gggggggccc | 1380 |

```
ctctgggggt tccgggctta ggtgcgcttg catggggggt caaagctctt ctaaaggtgc    1440
tccctaattt tggattcagt gggcggggggt tttagaggct ccgtgacctg ggaaaaaccc    1500
ctggggttta gccgcatctt aaatcggctt tggggggga attccccct tttgggggg      1560 ttggggggtta aatggcgcag ggggg                                         1585
```

<210> SEQ ID NO 7
<211> LENGTH: 828
<212> TYPE: DNA
<213> ORGANISM: Homo sapiens
<220> FEATURE: -
<223> OTHER INFORMATION: 1962202

<400> SEQUENCE: 7

```
aatttctaac ctttggttgc ctttagtcaa agaaagagct tagatttaca tgcacatgtt    60
taaaaaattc agcaaatcta tgactgccat aaactctgca tgacatacac agtgtcagca    120
agttactgct atgttaggct gtaaattatt cattccatac cttgcacaag aaaatatatt    180 cccttttta agaaagaaaa gttcacaact taggtgactg gaaatcaaag tattggcttc    240
taacctattt taaactaaga aatagtgatt tattaaatgt taaagttttc acaatttgat    300
gactagtccc ttttaaatat ccctataaa ttattagcaa tgatatcacc attctaaaat    360
gttataaatg taggaaacat tttgccttt gtagaaattc atgaaaatct tcatttcatg    420
gtggagtaat ttgagaaaga agcacagaaa agtagacttg gcaacaaatg ctatgaaatg    480
tgacttttgt atactcaaaa cagacgaacc tttaactaaa taactctaca ttaaccccca    540
aaattctgtt gaaaattctg tctttgtgcc ttcttaaatg taatattgag tatctaagat    600
ggaatggtca agtagcctca agtattttat taagagagaa aaataacagt ggctaacatt    660
ttaaatatat atcttcccaa ccacttaacc tttatacata tttttgttga aaataaacaa    720
tgggtctcct gagaagttgt atccagacca gagaaaggga agtttaaaga ataggcctac    780
acctattgtt tctcagaggt tgtgtttttg tttctttgt gggttttc                 828
```

<210> SEQ ID NO 8
<211> LENGTH: 1892
<212> TYPE: DNA
<213> ORGANISM: Homo sapiens
<220> FEATURE: -
<223> OTHER INFORMATION: 2083433

<400> SEQUENCE: 8

```
ctttttttgtg gtttcctgtg aagtgagcgt ttcccttgca catggctgct ttggtgcttt    60
ggcggctgtt ccaggggccg ttgcaaaacg ctcgtgcaag gagcacagct gcagccttgt    120
cctctgcagt aactcctccc agcacctctc tcacacccctt gttcccaaca gaacgtgttt    180
gtgcaactgt ccttggcctt tagaaatgac agctacactc tggaatctag aattaaccag    240
gctgaaaggg aacgcaacct gacagaggag aacactgaga agaactgga aaacttcaaa    300 gcttccatta cgtcctcagc ttcactctgg caccactgtg agcaccggga aacctaccag    360
aagttgctgg aggacatcgc tgtcctgcac cgcctggctg cccgcctctc cagccgagct    420
gaggtggtag cgcgcgtcca ccaggaaaag cgcatgtcga aagcaacgga agtgatgatg    480
cagtatgtgg agaatctaaa gaggacgtat gagaaggacc atgcggagct catggagttt    540
aaaaagcttg caaatcagaa ttcaagccgc agctgtggcc cctctgaaga tggggtccct    600
cgcacggcac ggtccatgtc cctcacgctg ggaaagaata tgcctcgccg gaggtcagcg    660
```

-continued

| | | |
|---|---|---|
| ttgctgtggt tcctaagttt aatgccctga atctgcctgg ccaaactccc agctcatcat | 720 |
| ccattccctc cttaccagcc ttgtcggaat cacccaatgg gaaaggcagc ctacctgtca | 780 |
| cttcagcact gcctgcactt ttggaaaatg gaaagacaaa tggggaccca gattgtgaag | 840 |
| cctctgctcc tgcgctgacc ctgagctgcc tggaggagct tagtcaggag accaaggcca | 900 |
| ggatggagga agaagcctac agcaagggat tccaagaagg tctaaagaag accaaagaac | 960 |
| ttcaagacct gaaggaggag gaggaagaac agaagagtga gagtcctgag gaacctgaag | 1020 |
| aggtagaaga aactgaggaa gaggaaaagg gcccaagaag cagcaaactt gaagaattgg | 1080 |
| tccatttctt acaagtcatg tatcccaaac tgtgtcagca ctggcaagtg atctggatga | 1140 |
| tggctgcagt gatgctggtc ttgactgttg tgctggggct ctacaattcc tataactctt | 1200 |
| gtgcagagca ggctgatggg cccttggaa gatccacttg ctcggcagcc cagagggact | 1260 |
| cctggtggag ctcaggactc cagcatgagc agcctacaga gcagtaggaa acctcacacc | 1320 |
| tagccagtgc cctgctctga gacactcaga ctaccaccct ttccccaagt ataacgtcag | 1380 |
| gcccaagtgt ggacacactg ccgcccatcc catcaggtca tgaggaaggg ttcttttaac | 1440 |
| actcggcact tctgtgggag ctattcatac acagtgactt gatgttcttg gaggatcaac | 1500 |
| aaaactgccc tgggaaagca tccagtggat gaagaagtca ccttcaccaa ggaactctat | 1560 |
| tggaagggaa ggtctcctgc ccctagctca ggtggctggg gagaactaaa acaccttcac | 1620 |
| tggtggttgg gggtaaggag cggggcacgg gggaggagga ggtaggggggc agtaaaaaac | 1680 |
| ttactctctt ttttcctctc tgtaattggt tatcaggaag aatttgctta atgactaaca | 1740 |
| ccctaagcat cagacctgga atttggagtt gcaaagtgac tatcttccca tttcccatct | 1800 |
| cattttcaat aacttcagcc tcccattctt tcctttggaa tgagagtttc tttttacaga | 1860 |
| agtaggaaag gcttctcaaa aaaaaaaaaa aa | 1892 |

<210> SEQ ID NO 9
<211> LENGTH: 2055
<212> TYPE: DNA
<213> ORGANISM: Homo sapiens
<220> FEATURE: -
<223> OTHER INFORMATION: 2227688

<400> SEQUENCE: 9

| | | |
|---|---|---|
| agagcaggcg tcgggacgca gcaaagagag gagagacccc agagtcagaa ggagtgagaa | 60 |
| ccctgacccc taatcccact gcatccagcc aataggagcc cagccaccat ggcggagctg | 120 |
| caggaggtgc agatcacaga ggagaagcca ctgttgccag acagacgcc tgaggcggcc | 180 |
| aaggaggctg agttagctgc ccgaatcctc ctggaccagg gacagactca ctctgtggag | 240 |
| acaccatacg gctctgtcac tttcactgtc tatggcaccc ccaaacccaa acgcccagcg | 300 |
| atccttacct accacgatgt gggactcaac tataaatctt gcttccagcc actgtttcag | 360 |
| ttcgaggaca tgcaggaaat cattcagaac tttgtgcggg ttcatgtgga tgcccctgga | 420 |
| atggaagagg gagcccctgt gttccctttg ggatatcagt acccatctct ggaccagctt | 480 |
| gcagacatga tcccttgcgt cctgcagtac ctaaatttct ctacaataat tggagttggt | 540 |
| gttggagctg gagcctacat cctggcgaga tatgctctta accacccgga cactgttgaa | 600 |
| ggtcttgtcc tcatcaacat tgatcccaat gccaagggtt ggatggattg gcagcccac | 660 |
| aagctaacag gcctcacctc ttccattccg gagatgatcc ttggacatct tttcagccag | 720 |
| gaaagagctct ctggaaattc tgagttgata caaaagtaca gaaatatcat tacacatgca | 780 |
| cccaacctgg ataacattga attgtactgg aacagctaca acaaccgccg agacctgaac | 840 |

-continued

```
tttgagcgtg gaggtgatat caccctcagg tgtcctgtga tgctggtggt aggagaccaa      900
gcacctcatg aagatgcagt ggtggaatgt aactcaaaac tggacccac ccagacctcg       960 ttcctcaaga tggctgactc cggaggtcag ccccagctga ctcagccagg caagctgacc     1020
gaggccttca agtacttcct gcaaggcatg ggctacatgg cctcatcctg catgactcgc     1080
ctgtcccggt ctcgtacagc ctctctgacc agtgcagcat ccgttgatgg caaccggtcc     1140
cgctctcgca ccctgtccca gagcagcgag tctggaactc tttcttcggg gccccggggg     1200
cacaccatgg aggtctcctg ttgaatggcc cttgttgccc tagagtggga cccagccctc     1260
acctccccca gagctaacct gggaggtgct gaagggggcat tgggccaccg taagcaaggg    1320 aaaagggca gatcatgcgg ggagatgacc ttgatctttg attgctaccc taaccttgac      1380
ctttaacccg tgattccccc cagctcctgg aagagatgtc ctaatatctc ttagggaccc     1440
agacccctaa attctcctcc tcccccattt tgatgttaag gtggagaggg catatgcatc     1500
ctctgtcctg atctaggtgt ctatagctga ggggtaagag gttgttgtag ttgtcctggt     1560
gcctccatca gactctccct acttgtccca tatttgcaag gggagggggat ttggggctgg    1620 ggctccattc accaaagctg aggtggcttc tcattaaccc tttaggactc tgaagggtat     1680
ggacctacgt gaatgtgtgt caggggagaa cttgctggtg ggtagtggt cctcaggatg      1740 tgatagaaac atccagtgta aaaggaagt tggaatggga gttggcgggc agtgaacgag      1800
tgtggggaag gattggtgct ggggcaacag gaaggggcct ggggccgttt ggctgcacta     1860
actttggtag ctcagtgtgc atctagagtg ggactgggga gggagctaag cttgggctgg    1920
gctgcttggg gcttggcata gggtggaaag ggctaccctg gggctctgac cacactgtag    1980
tatgtgtgga gggtgccctc ccgtctccca caacttctgc tataacaata aactgtagag    2040
gaatctgaaa aaaaa                                                      2055
```

<210> SEQ ID NO 10
<211> LENGTH: 2319
<212> TYPE: DNA
<213> ORGANISM: Homo sapiens
<220> FEATURE:
<221> NAME/KEY: unsure
<222> LOCATION: 20, 21, 23, 25, 26, 28, 32, 34
<223> OTHER INFORMATION: a or g or c or t, unknown, or other
<220> FEATURE: -
<223> OTHER INFORMATION: 2313925

<400> SEQUENCE: 10

```
caggtcgact ctagagcaan ngncnncnac cncnaccacc ccctccacca ccacgacagc       60
caggagctgc cccagccccc ttacagttct cctatcagac ttgtgagctg ccaagcgctg      120
cttcccctgc gccagactat cccactccct gtcagtatcc tgtggatgga gcccagcaga     180
gcgacctaac ggggccagac tgtcccagaa gcccaggact gcaagaggcc cctccagct     240 acgacccact agccctctct gagctacctg gactctttga ttgtgaaatg ctagacgctg     300
tggatccaca acacaacggg tatgtcctgg tgaattagtc tcagcacagg aattgaggtg     360
ggtcaggtga aggaagagtg tatgttccta tttttattcc agccttttaa atttaaagct    420
tattttcttg ccctctccct aacggggaga atcgagcca cccaactgga atcagagggt      480
ctggctgggg tggatgttgc ttcctcctgg ttctgcccca ccacaaagtt ttctgtggca    540
agtgctggaa catagttgta ggctgaggct cctgcccttc ggtcgagtgg agcaagctct    600
cgagggcagc actgacaaat gtgttcctaa gaagacattc agacccaggt cttatgcagg    660
```

```
attacatccg tttattatca agggcaacct tggtgaaagc agaaagggtg tgtgctattg    720
catatatatg ggggaaaagg caatatattt ttcactgaag ctgagcaacc acatattgct    780
acaaggcaaa tcaagaagac atcaggaaat cagatgcaca ggaaataaag gaaagctgtg    840 cttttgtcatt gaatcctaag ttcttagctg ctgatgcaag ttgtccccca aggccatcac   900
aaagcagtgg ggcatgagct gtgtttcagg ggccactaaa taacagctgg tactgacccc    960
agaaaccgcc ttcatctcca ttcggaagca ggtgacacac cccttcagaa ggtgccctgg   1020
gttgccgagt gtcagaatat actcaggact ccagaggtgt cacacgtgga actgacagga   1080
gacccgccac cgtggaggca gggggcaaga aactcaagaa cgcatcaaga gcaccagccc   1140
tgggccaggg aagacaggct cttcctgcag tttctcgtgg acactgctgg cttgcgggca   1200
gtcggtctcc agggtacctg ttgtctcttt tccgatgtaa taactacttt gaccttacac   1260
tatatgttgc tagtagttta ttgagctttg tatatttgga cagtttcata tagggcttag   1320
agattttaag gacatgataa atgaactttt ctgtcccatg tgaagtggta gtgcggtgcc   1380
tttcccccag atcatgcttt aattctttct tttctgtaga aaccaacagt ttccattat    1440 gtcaatgcta aatccaaagt cacttcagag tttgttttcc accatgtggg aatcagcatt   1500
cttaatttcg ttaaagtttt gacttgtaat gaaatgttca agtattacag caatattcaa   1560
agaaagaacc acagatgtgt taaccattta agcagatcat ctgccaaaca ttatattact   1620
aataaaactt aaccaacact tacaattcag tcatcaaagt aagtaaaaat tagatgctac   1680
agctagctaa ctgtatccct agaaatgatg aataatttgc catttggaca gttaacatcc   1740
aggtgttaca aagtcagtgt taattctaaa gatgatcatt tctgcccttt agaatggctt   1800
gtcccatcag cagatgaatg tgttaagcac aaagcatctt ccttaaagca caagagagg    1860 gactaactga tgctgcatct agaaaacacc tttaagttgc ctttcctctt tgtagttagc   1920
gttcaggcag gtgacgtgtg gaaagtctag ggggttccat tctggccatg cgagcccagc   1980
tcctaccaac gtcggtaact tgagcagtcc ctgttgctgg ccagagactg cctggtcgcc   2040
agcgctcacc atgggtgcca ggatgcttcg cagaggcact gtgctcacgg ttggacttgg   2100
tgtcagtggg aaagggcagt gtggggactg tcattttttgt gatttaataa cacacagtga   2160
aaatccagga agaatgaatt aagcttcttc tgggagttgt ttattcctgc tcgtgcttaa   2220
gattgatgat ttcgtgaaat aaagaacaat catttcattt atgagatcat ttcattaaga   2280
tctctaatct gttttgagtc tttacaaaat agccagtta                           2319
```

<210> SEQ ID NO 11
<211> LENGTH: 668
<212> TYPE: DNA
<213> ORGANISM: Homo sapiens
<220> FEATURE: -
<223> OTHER INFORMATION: 2507107

<400> SEQUENCE: 11

```
gcttcttctt tcttctgctc ataaaaggag gaacacttta gatagagggc aaatatatct     60
gaaaacctaa tttctttctt ttttgataa ggaaatcttt tccatctcca tcctaacatg    120
cacaacctgt gaagagaatt gtttctatag taactggtct gtgatctttt gtggccaaga    180
gaatagcagg caagaattag ggccttgaca gaatttccac gaagctctga aacatgttt    240 gtttcgaatg tctgattcct ctttgtcatc aatgtgtatg ctctgtcccc atccttcact    300
cctcctcaag ctcacaccaa ttggtttggc acaggcacag agctggtccc tagttaagtg    360
gcatttatgt taaaaaaaaa tagttcagaa tctcagcctt ttcttttgtgt catcaaaaca    420
```

```
gcttaagaag gggactactg ccaatgtcct ctagtctgac ctccacccag ggaggaccca    480
tggcaggtct tttcaacttt ctgattcatg agaacaacct tgtgaagctt ttcccacctc    540
ctaaagtgtt ttctgcatct gttccttcct ttggacctca caacaaatcc tgtgaagtaa    600
ctgagacatc tgttgttaga tacatttttg tgatgagtaa actgaggctt cgtgattcaa    660
aaaaaaaa                                                             668
```

<210> SEQ ID NO 12
<211> LENGTH: 2112
<212> TYPE: DNA
<213> ORGANISM: Homo sapiens
<220> FEATURE:
<221> NAME/KEY: unsure
<222> LOCATION: 4, 9, 13, 27, 35, 37, 62, 88, 95, 102, 120, 173
<221> NAME/KEY: unsure
<222> LOCATION:
<223> OTHER INFORMATION: a or g or c or t, unknown, or other
<220> FEATURE: -
<223> OTHER INFORMATION: 2544503

<400> SEQUENCE: 12

```
aacnaattng ggnccccggtt ttcgggnatt tggtngnggt ttaggagtgg gccttttttca    60 ancttccctg gtaggagact tcccttgntg gaaancaact cntaaacttc caggcctccn    120
cccaagctca ctttatttaa tgcaaattcc accaaatcaa gagtggggaa tcnaagcaaa    180
tgcattcaaa aaactggata acctcacctt cctctacttg gaccataatg ccctggaatc    240
cgtgcctctt aatttaccag aaagtctacg tgtaattcat cttcagttca acaacatagc    300
ttcaattaca gatgacacat tctgcaaggc taatgacacc agttacatcc gggaccgcat    360
tgaagagata cgcctggagg gcaatccaat cgtcctggga aagcatccaa acagttttat    420
ttgcttaaaa agattaccga tagggtcata cttttaacct ctattggtac aacatataaa    480
tgaaagtaca cctacactaa tagtctgtct caacaatgtg taaggaact taagtattgg    540 tttaatatta accttgtatc tcattttgaa ggaatttaat attttaagca aggatgttca    600
aaatcttaca tataataagt aaaaagtaag actgaatgtc tacgttcgaa acaaagtaat    660
atgaaaatat ttaaacagca ttacaaaatc ctagtttata ctagactacc atttaaaaat    720 catgtttta tataaatgcc caaatttgag atgcattatt cctattacta atgatgtaag    780
tacgaggata aatccaagaa actttcaact cttttgcctt tcctggcctt tactggatccc   840 aaaagcattt aaggtacatg ttccaaaaac tttgaaaagc taaatgtttc ccatgatcgc    900
tcattcttct tttatgattc atacgttatt cctataaag taagaacttt gttttcctcc    960
tatcaaggca gctattttat taaattttc acttagtctg agaaatagca gatagtctca    1020
tatttaggaa aactttccaa ataaaataaa tgttattctc tgataaagag ctaatacaga    1080
aatgttcaag ttattttact ttctggtaat gtcttcagta aaatattttc tttatctaaa    1140
tattaacatt ctaagtctac caaaaaaagt tttaaactca agcaggccaa accaatatg    1200 cttataagaa ataatgaaaa gttcatccat ttctgataaa gttctctatg gcaaagtctt    1260
tcaaatacga gataactgca aaatattttc cttttatact acagaaatga gaatctcatc    1320
aataaattag ttcaagcata agatgaaaac agaaatattct gtggtgccag tgcacactac    1380
cttcccaccc atacacatcc atgttcactg taacaaactg aatattcaca ataaagcttc    1440
tgagtaacac tttctgatta ctcatgataa actgacatgg ctaactgcaa gaattaaatc    1500
ttctatctga gagtaataat ttatgatgac tcagtggtgc cagagtaaag tttctaaaat    1560
```

-continued

```
aacattcctc tcacttgtac cccactaaaa gtattagtct acacattaca ttgaagttaa    1620
acacaaaatt atcagtgttt tagaaacatg agtccggact gtgtaagtaa aagtacaaac    1680
attatttcca ccataaagta tgtattgaaa tcaagttgtc tctgtgtaca gaatacatac    1740
ttattcccat ttttaagcat ttgcttctgt tttccctacc tagaatgtca gatgttttc    1800 agttatctcc ccatttgtca aagttgacct caagataaca ttttttcatta aagcatctga   1860 gatctaagaa cacaattatt attctaacaa tgattattag ctcattcact tattttgata   1920
actaatgatc acagctatta tactactttc tcgttatttt gtgtgcatgc ctcatttccc   1980
tgacttaaac ctcactgaga gcgcaaaatg cagctttata cttttactt tcaattgcct    2040 agcacaatag tgagtacatt tgaattgaat atataataaa tattgcaaaa taaaatccat   2100
ctaaataaaa aa                                                        2112
```

<210> SEQ ID NO 13
<211> LENGTH: 2029
<212> TYPE: DNA
<213> ORGANISM: Homo sapiens
<220> FEATURE: -
<223> OTHER INFORMATION: 3044710

<400> SEQUENCE: 13

```
ccttgacaag tcagaagctt gaaagcaggg aaatccggat gtctcggtta tgaagtggag     60
cagtgagtgt gagcctcaac atagttccag aactctccat ccggactagt tattgagcat    120
ctgcctctca tatcaccagt ggccatctga ggtgtttccc tggctctgaa ggggtaggca    180
cgatggccag gtgcttcagc ctggtgttgc ttctcacttc catctggacc acgaggctcc    240
tggtccaagg ctctttgcgt gcagaagagc tttccatcca ggtgtcatgc agaattatgg    300
ggatcaccct tgtgagcaaa aaggcgaacc agcagctgaa tttcacagaa gctaaggagg    360
cctgtaggct gctgggacta agtttggccg gcaaggacca agttgaaaca gccttgaaag    420
ctagctttga aacttgcagc tatggctggg ttggagatgg attcgtggtc atctctagga    480
ttagcccaaa ccccaagtgt gggaaaaatg gggtgggtgt cctgatttgg aaggttccag    540
tgagccgaca gttttgcagcc tattgttaca actcatctga tacttggact aactcgtgca    600
ttccagaaat tatcaccacc aaagatccca tattcaacac tcaaactgca acacaaacaa    660
cagaatttat tgtcagtgac agtacctact cggtggcatc cccttactct acaatacctg    720
cccctactac tactcctcct gctccagctt ccacttctat tccacggaga aaaaaattga    780
tttgtgtcac agaagttttt atggaaacta gcaccatgtc tacagaaact gaaccatttg    840
ttgaaaataa agcagcattc aagaatgaag ctgctgggtt tggaggtgtc cccacggctc    900
tgctagtgct tgctctcctc ttctttggtg ctgcagctgg tcttggatttt gctatgtca    960 aaaggtatgt gaaggccttc ccttttacaa acaagaatca gcagaaggaa atgatcgaaa   1020
ccaaagtagt aaaggaggag aaggccaatg atagcaaccc taatgaggaa tcaaagaaaa   1080
ctgataaaaa cccagaagag tccaagagtc aagcaaaac taccgtgcga tgcctggaag    1140
ctgaagttta gatgagacag aaatgaggag acacacctga ggctggtttc tttcatgctc   1200
cttaccctgc cccagctggg gaaatcaaaa gggccaaaga accaagaag aaagtccacc    1260 cttggttcct aactggaatc agctcaggac tgccattgga ctatggagtg caccaaagag   1320
aatgcccttc tccttattgt aaccctgtct ggatcctatc ctcctacctc caaagcttcc   1380
cacggccttt ctagcctggc tatgtcctaa taatatccca ctgggagaaa ggagttttgc   1440
aaagtgcaag gacctaaaac atctcatcag tatccagtgg taaaaaggcc tcctggctgt    1500
```

-continued

```
ctgaggctag gtgggttgaa agccaaggag tcactgagac caaggctttc tctactgatt    1560
ccgcagctca gacctttct tcagctctga aagagaaaca cgtatcccac ctgacatgtc      1620
cttctgagcc cggtaagagc aaaagaatgg cagaaaagtt tagcccctga aagccatgga    1680
gattctcata acttgagacc taatctctgt aaagctaaaa taaagaaata gaacaaggct    1740
gaggatacga cagtacactg tcagcaggga ctgtaaacac agacagggtc aaagtgtttt    1800
ctctgaacac attgagttgg aatcactgtt tagaacacac acacttactt tttctggtct    1860
ctaccactgc tgatattttc tctaggaaat atacttttac aagtaacaaa ataaaaact     1920 cttataaatt tctatttta tctgagttac agaaatgatt actaaggaag attactcagt     1980
aatttgttta aaagtaata aaattcaaca aacatttaaa aaaaaaaa                  2029
```

<210> SEQ ID NO 14
<211> LENGTH: 1726
<212> TYPE: DNA
<213> ORGANISM: Homo sapiens
<220> FEATURE:
<221> NAME/KEY: unsure
<222> LOCATION: 1213, 1353, 1366, 1459, 1460, 1463, 1469, 1482, 1512,
      1524,
<221> NAME/KEY: unsure
<222> LOCATION: 1557, 1567, 1583, 1599, 1619, 1638, 1649, 1662, 1696,
      1708,
<221> NAME/KEY: unsure
<222> LOCATION: 1715
<223> OTHER INFORMATION: a or g or c or t, unknown, or other
<220> FEATURE: -
<223> OTHER INFORMATION: 3507515

<400> SEQUENCE: 14

```
aggcgccgta ggctggaagc gccagcgctg ccggcgggcg gtgtgattga tccgcgtccc    60
ctggagctgg aggctcgggg gaaagggcca gcacggagcg ggcgctcggt tgctgcgcac    120
aaaggctgag gctccaagag ctgcagggcg tgtttgggac cccagagtca gaaggagtga    180
gaaccctgac ccctaatccc actgcatcca gccaatagga gcccagccac catggcggag    240
ctgcaggagg tgcagatcac agaggagaag ccactgttgc caggacagac gcctgaggcg    300
gccaagactc actctgtgga gacaccatac ggctctgtca cttttcactgt ctatggcacc    360 cccaaaccca acgcccagc gatccttacc taccacgatg tgggactcaa ctataaatct    420
tgcttccagc cactgtttca gttcgaggac atgcaggaaa tcattcagaa ctttgtgcgg    480
gttcatgtgg atgcccctgg aatggaagag ggagcccctg tgttcccttt gggatatcag    540
tacccatctc tggaccagct tgcagacatg atcccttgcg tcctgcagta cctaaatttc    600
tctacaataa ttggagttgg tgttggagct ggagcctaca tcctggcgag atatgctctt    660
aaccacccgg acactgttga aggtcttgtc ctcatcaaca ttgatcccaa tgccaagggt    720
tggatggatt gggcagccca caagctaaca ggcctcacct cttccattcc ggagatgatc    780
cttggacatc ttttcagcca ggaagagctc tctggaaatt ctgagttgat acaaaagtac    840
agaaatatca ttacacatgc acccaacctg ataacattg aattgtactg gaacagctac    900
aacaaccgcc gagacctgaa ctttgagcgt ggaggtgata tcaccctcag gtgtcctgtg    960
atgctggtgg taggagacca agcacctcat gaagatgcag tggtgaatg taactcaaaa    1020 ctggaccca cccagacctc gttcctcaag atggctgact ccggaggtca gccccagctg    1080
actcagccag gcaagctgac cgaggccttc aagtacttcc tgcaaggcat gggctacatg    1140
gcctcatcct gcatgactcg cctgtcccgg tctcgtacag cctctctgac cagtgcagca    1200
```

-continued

| | |
|---|---|
| tccgttgatg gcnaccggtc ccgctctcgc accctgtccc agagcagcga gtctggaact | 1260 |
| cttttcttcg ggggcccccg ggggcacacc atgggaggtc tcctgttgaa tggcccttgt | 1320 |
| tgccctagag tgggacccag ccctcagctc ccncagagta acctgngagg tgctgaaagg | 1380 |
| gggcattggg gccaccgtaa gcaaagggga aaaagggcag attcatggcg ggggagatga | 1440 |
| ccttgattct ttgaattgnn aancctaanc ttgaacttta anccgtgatt cccccccagc | 1500 |
| tcctgggaag angaggtcct aatnatctct taagggaccc cagaacccct aaaattnctc | 1560 |
| cgtcttnccc cattttgaag gtnaaagggg aaaaggggna tatggaatcc tctgttccng | 1620 |
| gatttaaggg gtccaaangt tgagggggna aaaggttgtg gnaattggtc cctggtggct | 1680 |
| ccatcaagaa tttccnaaat tgtcccanat tttgnaaggg ggggt | 1726 |

<210> SEQ ID NO 15
<211> LENGTH: 757
<212> TYPE: DNA
<213> ORGANISM: Homo sapiens
<220> FEATURE:
<221> NAME/KEY: unsure
<222> LOCATION: 596, 606, 613, 636, 639, 655, 659, 671, 676, 677, 682, 700,
<221> NAME/KEY: unsure
<222> LOCATION: 708, 710, 728, 731, 742, 755
<223> OTHER INFORMATION: a or g or c or t, unknown, or other
<220> FEATURE: -
<223> OTHER INFORMATION: 3540909

<400> SEQUENCE: 15

| | |
|---|---|
| ggaggcgctt cggctccgga ctacgctcct gctgtgcgct cgcggggcca gcagtgctgg | 60 |
| cttctgcagt aggaggcgcg ggggcatggc gcagaggctg ggcgagtggg cccgggggcc | 120 |
| ctccgatgcc accgggctct accgggctgt gctgctccgg tcggccgcca tgtacttcgg | 180 |
| agatccagag ggagcgggca gacattgggg gcctgatggc ccggccagaa tacagagagt | 240 |
| ggaatccgga gctcatcaag cccaagaagc tgctgaaccc cgtgaaggcc tctcggagtc | 300 |
| accaggagct ccaccgggag ctgctcatga accacagaag gggccttggt gtggacagca | 360 |
| agccagagct gcagcgtgtc ctagagcacc gccggcggaa ccagctcatc aagaagaaga | 420 |
| aggaggagct ggaagccaag cggctgcagt gccccttga gcaggagctg ctgagacggc | 480 |
| agcagaggct gaaccagctg gaaaaaccac cagagaagga agaggatcac gcccccgagt | 540 |
| ttattaaagt cagggaaaac ctgcggagaa ttgccacact gaaccagcga agaganagag | 600 |
| ttttanggcc agntgccggg ctcaaggcca ttgccnacnt tgggcttgaa aatcnttcnt | 660 |
| taagcctttc ngtacnngga anccttgggg ccccaggccn tgggaacntn tgagattttc | 720 |
| ccaactgntt ntgtagaaat gngcaccccc cgttntt | 757 |

<210> SEQ ID NO 16
<211> LENGTH: 2430
<212> TYPE: DNA
<213> ORGANISM: Homo sapiens
<220> FEATURE: -
<223> OTHER INFORMATION: 3688209

<400> SEQUENCE: 16

| | |
|---|---|
| gcgctcctct agctgggagg tggaagcagc attgcccaag cctcccagga gtgacaggaa | 60 |
| ttgtttctgc ctgaggagac actctgcagc ctgggctctg tgagactgag gtggcggtca | 120 |
| gccggagtga gtgtttgggt cctggggcac ctgccttaca tggcttgttt atgaacatta | 180 |
| aagggaagaa gttgaagctt gaggagcgag gatggcagtc aacaaaggcc tcaccttgct | 240 |
| ggatggagac ctccctgagc aggagaatgt gctgcagcgg gtcctgcagc tgccggtggt | 300 |

-continued

```
gagtggcacc tgcgaatgct tccagaagac ctacaccagc actaaggaag cccaccccct    360
ggtggcctct gtgtgcaatg cctatgagaa gggcgtgcag agcgccagta gcttggctgc    420
ctggagcatg gagccggtgg tccgcaggct gtccacccag ttcacagctg ccaatgagct    480
ggcctgccga ggcttggacc acctggagga aaagatcccc gccctccagt accccccctga   540 aaagattgct tctgagctga aggacaccat ctccacccgc ctccgcagtg ccagaaacag    600
catcagcgtt cccatcgcga gcacttcaga caaggtcctg ggggccgctt tggccgggtg    660
cgagcttgcc tggggggtgg ccagagacac tgcggaattt gctgccaaca ctcgagctgg    720
ccgactggct tctggagggg ccgacttggc cttgggcagc attgagaagg tggtggagta    780
cctcctccct gcagacaagg aagagtcagc ccctgctcct ggacaccagc aagcccagaa    840
gtctcccaag gccaagccaa gcctcttgag cagggttggg gctctgacca acaccctctc    900
tcgatacacc gtgcagacca tggcccgggc cctggagcag ggccacaccg tggccatgtg    960
gatcccaggc gtggtgcccc tgagcagcct ggcccagtgg ggtgcctcag tggccatgca   1020
ggcggtgtcc cggcggagga gcgaagtgcg ggtaccctgg ctgcacagcc tcgcagccgc   1080
ccaggaggag gatcatgagg accagacaga cacggaggga gaggacacgg aggaggagga   1140
agaattggag actgaggaga acaagttcag tgaggtagca gccctgccag ccctcgagg    1200 cctcctgggt ggtgtggcac ataccctgca gaagaccctc cagaccacca tctcggctgt   1260
gacatgggca cctgcagctg tgctgggcat ggcagggagg gtgctgcacc tcacaccagc   1320
ccccgctgtc tcctcaacca aggggagggc catgtcccta tcagatgccc tgaagggcgt   1380
tactgacaac gtggtggaca cagtggtgca ttacgtgccg ctccccaggc tgtcgctgat   1440
ggagcccgag agcgaattcc gggacatcga caacccacca gccgaggtcg agcgccggga   1500
ggcggagcgc agagcgtctg gggcgccgtc cgccggcccg gagcccgccc cgcgtctcgc   1560
acagccccgc cgcagcctgc gcagcgcgca gagccccggc gcgccccccg gcccgggcct   1620
ggaggacgaa gtcgccacgc ccgcagcgcc gcgcccgggc ttccggccg tgccccgcga    1680 gaagccaaag cgcagggtca gcgacagctt cttccggccc agcgtcatgg agcccatcct   1740
gggccgcacg cattacagcc agctgcgcaa gaagagctga gtcgccgcac cagccgccgc   1800
gccccgggcc ggcgggtttc tctaacaaat aaacagaacc cgcactgccc aggcgagcgt   1860
tgccactttc aaagtggtcc cctgggggagc tcagcctcat cctgatgatg ctgccaaggc   1920
gcacttttta ttttatttt attttttattt tttttttagc atccttttgg ggcttcactc   1980
tcagagccag tttttaaggg acaccagagc cgcagcctgc tctgattcta tggcttggtt   2040
gttactataa gagtaattgc ctaacttgat ttttcatctc tttaaccaaa cttgtggcca   2100
aaagatattt gaccgtttcc aaaattcaga ttctgcctct gcggataaat atttgccacg   2160
aatgagtaac tccgtcacc actctgaagg tccagacaga aggttttgac acattcttag    2220
cactgaactc ctctgtgatc taggatgatc tgttccccct ctgatgaaca tcctctgatg   2280
atctaggctc ccagcaggct actttgaagg gaacaatcag atggcaaaag ctcttgggtg   2340
tttatttaaa atactagtgt cactatctga gtacccgccg cttcacaggc tgagtccagc   2400
ctgtgtgcta tgtagagcag ctgcttgctc                                   2430
```

<210> SEQ ID NO 17
<211> LENGTH: 298
<212> TYPE: PRT
<213> ORGANISM: Homo sapiens
<220> FEATURE: -

<223> OTHER INFORMATION: 159452

<400> SEQUENCE: 17

Met Lys Thr Leu Gln Ser Thr Leu Leu Leu Leu Val Pro
1               5                   10                  15

Leu Ile Lys Pro Ala Pro Thr Gln Gln Asp Ser Arg Ile Ile
            20                  25                  30

Tyr Asp Tyr Gly Thr Asp Asn Phe Glu Glu Ser Ile Phe Ser Gln
                35                  40                  45

Asp Tyr Glu Asp Lys Tyr Leu Asp Gly Lys Asn Ile Lys Glu Lys
            50                  55                  60

Glu Thr Val Ile Ile Pro Asn Glu Lys Ser Leu Gln Leu Gln Lys
            65                  70                  75

Asp Glu Ala Ile Thr Pro Leu Pro Pro Lys Lys Glu Asn Asp Glu
            80                  85                  90

Met Pro Thr Cys Leu Leu Cys Val Cys Leu Ser Gly Ser Val Tyr
            95                  100                 105

Cys Glu Glu Val Asp Ile Asp Ala Val Pro Pro Leu Pro Lys Glu
            110                 115                 120

Ser Ala Tyr Leu Tyr Ala Arg Phe Asn Lys Ile Lys Lys Leu Thr
            125                 130                 135

Ala Lys Asp Phe Ala Asp Ile Pro Asn Leu Arg Arg Leu Asp Phe
            140                 145                 150

Thr Gly Asn Leu Ile Glu Asp Ile Glu Asp Gly Thr Phe Ser Lys
            155                 160                 165

Leu Ser Leu Leu Glu Glu Leu Ser Leu Ala Glu Asn Gln Leu Leu
            170                 175                 180

Lys Leu Pro Val Leu Pro Pro Lys Leu Thr Leu Phe Asn Ala Lys
            185                 190                 195

Tyr Asn Lys Ile Lys Ser Arg Gly Ile Lys Ala Asn Ala Phe Lys
            200                 205                 210

Lys Leu Asn Asn Leu Thr Phe Leu Tyr Leu Asp His Asn Ala Leu
            215                 220                 225

Glu Ser Val Pro Leu Asn Leu Pro Glu Ser Leu Arg Val Ile His
            230                 235                 240

Leu Gln Phe Asn Asn Ile Ala Ser Ile Thr Asp Asp Thr Phe Cys
            245                 250                 255

Lys Ala Asn Asp Thr Ser Tyr Ile Arg Asp Arg Ile Glu Glu Ile
            260                 265                 270

Arg Leu Glu Gly Asn Pro Ile Val Leu Gly Lys His Pro Asn Ser
            275                 280                 285

Phe Ile Cys Leu Lys Arg Leu Pro Ile Gly Ser Tyr Phe
            290                 295

<210> SEQ ID NO 18
<211> LENGTH: 154
<212> TYPE: PRT
<213> ORGANISM: Homo sapiens
<220> FEATURE: -
<223> OTHER INFORMATION: 1299627

<400> SEQUENCE: 18

Met Asp Ala Pro Arg Leu Pro Val Arg Pro Gly Val Leu Leu Pro
1               5                   10                  15

Lys Leu Val Leu Leu Phe Val Tyr Ala Asp Asp Cys Leu Ala Gln
            20                  25                  30

```
Cys Gly Lys Asp Cys Lys Ser Tyr Cys Cys Asp Gly Thr Thr Pro
             35                  40                  45

Tyr Cys Cys Ser Tyr Tyr Ala Tyr Ile Gly Asn Ile Leu Ser Gly
             50                  55                  60

Thr Ala Ile Ala Gly Ile Val Phe Gly Ile Val Phe Ile Met Gly
             65                  70                  75

Val Ile Ala Gly Ile Ala Ile Cys Ile Cys Met Cys Met Lys Asn
             80                  85                  90

His Arg Ala Thr Arg Val Gly Ile Leu Arg Thr Thr His Ile Asn
             95                 100                 105

Thr Val Ser Ser Tyr Pro Gly Pro Pro Tyr Gly His Asp His
            110                 115                 120

Glu Met Glu Tyr Cys Ala Asp Leu Pro Pro Pro Tyr Ser Pro Thr
            125                 130                 135

Pro Gln Gly Pro Ala Gln Arg Ser Pro Pro Pro Tyr Pro Gly
            140                 145                 150

Asn Ala Arg Lys

<210> SEQ ID NO 19
<211> LENGTH: 371
<212> TYPE: PRT
<213> ORGANISM: Homo sapiens
<220> FEATURE: -
<223> OTHER INFORMATION: 2227688

<400> SEQUENCE: 19

Met Ala Glu Leu Gln Glu Val Gln Ile Thr Glu Glu Lys Pro Leu
  1               5                  10                  15

Leu Pro Gly Gln Thr Pro Glu Ala Ala Lys Glu Ala Glu Leu Ala
             20                  25                  30

Ala Arg Ile Leu Leu Asp Gln Gly Gln Thr His Ser Val Glu Thr
             35                  40                  45

Pro Tyr Gly Ser Val Thr Phe Thr Val Tyr Gly Thr Pro Lys Pro
             50                  55                  60

Lys Arg Pro Ala Ile Leu Thr Tyr His Asp Val Gly Leu Asn Tyr
             65                  70                  75

Lys Ser Cys Phe Gln Pro Leu Phe Gln Phe Glu Asp Met Gln Glu
             80                  85                  90

Ile Ile Gln Asn Phe Val Arg Val His Val Asp Ala Pro Gly Met
             95                 100                 105

Glu Glu Gly Ala Pro Val Phe Pro Leu Gly Tyr Gln Tyr Pro Ser
            110                 115                 120

Leu Asp Gln Leu Ala Asp Met Ile Pro Cys Val Leu Gln Tyr Leu
            125                 130                 135

Asn Phe Ser Thr Ile Ile Gly Val Gly Val Gly Ala Gly Ala Tyr
            140                 145                 150

Ile Leu Ala Arg Tyr Ala Leu Asn His Pro Asp Thr Val Glu Gly
            155                 160                 165

Leu Val Leu Ile Asn Ile Asp Pro Asn Ala Lys Gly Trp Met Asp
            170                 175                 180

Trp Ala Ala His Lys Leu Thr Gly Leu Thr Ser Ser Ile Pro Glu
            185                 190                 195

Met Ile Leu Gly His Leu Phe Ser Gln Glu Glu Leu Ser Gly Asn
            200                 205                 210
```

```
Ser Glu Leu Ile Gln Lys Tyr Arg Asn Ile Ile Thr His Ala Pro
            215                 220                 225

Asn Leu Asp Asn Ile Glu Leu Tyr Trp Asn Ser Tyr Asn Asn Arg
            230                 235                 240

Arg Asp Leu Asn Phe Glu Arg Gly Gly Asp Ile Thr Leu Arg Cys
            245                 250                 255

Pro Val Met Leu Val Val Gly Asp Gln Ala Pro His Glu Asp Ala
            260                 265                 270

Val Val Glu Cys Asn Ser Lys Leu Asp Pro Thr Gln Thr Ser Phe
            275                 280                 285

Leu Lys Met Ala Asp Ser Gly Gly Gln Pro Gln Leu Thr Gln Pro
            290                 295                 300

Gly Lys Leu Thr Glu Ala Phe Lys Tyr Phe Leu Gln Gly Met Gly
            305                 310                 315

Tyr Met Ala Ser Ser Cys Met Thr Arg Leu Ser Arg Ser Arg Thr
            320                 325                 330

Ala Ser Leu Thr Ser Ala Ala Ser Val Asp Gly Asn Arg Ser Arg
            335                 340                 345

Ser Arg Thr Leu Ser Gln Ser Glu Ser Gly Thr Leu Ser Ser
            350                 355                 360

Gly Pro Pro Gly His Thr Met Glu Val Ser Cys
            365                 370

<210> SEQ ID NO 20
<211> LENGTH: 75
<212> TYPE: PRT
<213> ORGANISM: Homo sapiens
<220> FEATURE: -
<223> OTHER INFORMATION: 2507107

<400> SEQUENCE: 20

Met Ser Ser Ser Leu Thr Ser Thr Gln Gly Gly Pro Met Ala Gly
  1               5                  10                  15

Leu Phe Asn Phe Leu Ile His Glu Asn Asn Leu Val Lys Leu Phe
             20                  25                  30

Pro Pro Pro Lys Val Phe Ser Ala Ser Val Pro Ser Phe Gly Pro
             35                  40                  45

His Asn Lys Ser Cys Glu Val Thr Glu Thr Ser Val Val Arg Tyr
             50                  55                  60

Ile Phe Val Met Ser Lys Leu Arg Leu Arg Asp Ser Lys Lys Lys
             65                  70                  75

<210> SEQ ID NO 21
<211> LENGTH: 322
<212> TYPE: PRT
<213> ORGANISM: Homo sapiens
<220> FEATURE: -
<223> OTHER INFORMATION: 3044710

<400> SEQUENCE: 21

Met Ala Arg Cys Phe Ser Leu Val Leu Leu Leu Thr Ser Ile Trp
  1               5                  10                  15

Thr Thr Arg Leu Leu Val Gln Gly Ser Leu Arg Ala Glu Glu Leu
             20                  25                  30

Ser Ile Gln Val Ser Cys Arg Ile Met Gly Ile Thr Leu Val Ser
             35                  40                  45

Lys Lys Ala Asn Gln Gln Leu Asn Phe Thr Glu Ala Lys Glu Ala
             50                  55                  60
```

```
Cys Arg Leu Leu Gly Leu Ser Leu Ala Gly Lys Asp Gln Val Glu
                65                  70                  75

Thr Ala Leu Lys Ala Ser Phe Glu Thr Cys Ser Tyr Gly Trp Val
                80                  85                  90

Gly Asp Gly Phe Val Val Ile Ser Arg Ile Ser Pro Asn Pro Lys
                95                 100                 105

Cys Gly Lys Asn Gly Val Gly Val Leu Ile Trp Lys Val Pro Val
               110                 115                 120

Ser Arg Gln Phe Ala Ala Tyr Cys Tyr Asn Ser Ser Asp Thr Trp
               125                 130                 135

Thr Asn Ser Cys Ile Pro Glu Ile Ile Thr Thr Lys Asp Pro Ile
               140                 145                 150

Phe Asn Thr Gln Thr Ala Thr Gln Thr Thr Glu Phe Ile Val Ser
               155                 160                 165

Asp Ser Thr Tyr Ser Val Ala Ser Pro Tyr Ser Thr Ile Pro Ala
               170                 175                 180

Pro Thr Thr Thr Pro Pro Ala Pro Ala Ser Thr Ser Ile Pro Arg
               185                 190                 195

Arg Lys Lys Leu Ile Cys Val Thr Glu Val Phe Met Glu Thr Ser
               200                 205                 210

Thr Met Ser Thr Glu Thr Glu Pro Phe Val Glu Asn Lys Ala Ala
               215                 220                 225

Phe Lys Asn Glu Ala Ala Gly Phe Gly Gly Val Pro Thr Ala Leu
               230                 235                 240

Leu Val Leu Ala Leu Leu Phe Phe Gly Ala Ala Ala Gly Leu Gly
               245                 250                 255

Phe Cys Tyr Val Lys Arg Tyr Val Lys Ala Phe Pro Phe Thr Asn
               260                 265                 270

Lys Asn Gln Gln Lys Glu Met Ile Glu Thr Lys Val Val Lys Glu
               275                 280                 285

Glu Lys Ala Asn Asp Ser Asn Pro Asn Glu Gly Ser Lys Lys Thr
               290                 295                 300

Asp Lys Asn Pro Glu Glu Ser Lys Ser Pro Ser Lys Thr Thr Val
               305                 310                 315

Arg Cys Leu Glu Ala Glu Val
               320

<210> SEQ ID NO 22
<211> LENGTH: 402
<212> TYPE: PRT
<213> ORGANISM: Homo sapiens
<220> FEATURE:
<221> NAME/KEY: unsure
<222> LOCATION: 328, 374, 379
<223> OTHER INFORMATION: unknown, or other
<220> FEATURE: -
<223> OTHER INFORMATION: 3507515

<400> SEQUENCE: 22

Met Ala Glu Leu Gln Glu Val Gln Ile Thr Glu Glu Lys Pro Leu
 1               5                  10                  15

Leu Pro Gly Gln Thr Pro Glu Ala Ala Lys Thr His Ser Val Glu
                20                  25                  30

Thr Pro Tyr Gly Ser Val Thr Phe Thr Val Tyr Gly Thr Pro Lys
                35                  40                  45

Pro Lys Arg Pro Ala Ile Leu Thr Tyr His Asp Val Gly Leu Asn
```

```
                    50                  55                  60
Tyr Lys Ser Cys Phe Gln Pro Leu Phe Gln Phe Glu Asp Met Gln
                65                  70                  75
Glu Ile Ile Gln Asn Phe Val Arg Val His Val Asp Ala Pro Gly
            80                  85                  90
Met Glu Glu Gly Ala Pro Val Phe Pro Leu Gly Tyr Gln Tyr Pro
                95                 100                 105
Ser Leu Asp Gln Leu Ala Asp Met Ile Pro Cys Val Leu Gln Tyr
            110                 115                 120
Leu Asn Phe Ser Thr Ile Ile Gly Val Gly Val Gly Ala Gly Ala
                125                 130                 135
Tyr Ile Leu Ala Arg Tyr Ala Leu Asn His Pro Asp Thr Val Glu
            140                 145                 150
Gly Leu Val Leu Ile Asn Ile Asp Pro Asn Ala Lys Gly Trp Met
                155                 160                 165
Asp Trp Ala Ala His Lys Leu Thr Gly Leu Thr Ser Ser Ile Pro
            170                 175                 180
Glu Met Ile Leu Gly His Leu Phe Ser Gln Glu Glu Leu Ser Gly
                185                 190                 195
Asn Ser Glu Leu Ile Gln Lys Tyr Arg Asn Ile Ile Thr His Ala
            200                 205                 210
Pro Asn Leu Asp Asn Ile Glu Leu Tyr Trp Asn Ser Tyr Asn Asn
                215                 220                 225
Arg Arg Asp Leu Asn Phe Glu Arg Gly Gly Asp Ile Thr Leu Arg
            230                 235                 240
Cys Pro Val Met Leu Val Val Gly Asp Gln Ala Pro His Glu Asp
                245                 250                 255
Ala Val Val Glu Cys Asn Ser Lys Leu Asp Pro Thr Gln Thr Ser
            260                 265                 270
Phe Leu Lys Met Ala Asp Ser Gly Gly Gln Pro Gln Leu Thr Gln
                275                 280                 285
Pro Gly Lys Leu Thr Glu Ala Phe Lys Tyr Phe Leu Gln Gly Met
            290                 295                 300
Gly Tyr Met Ala Ser Ser Cys Met Thr Arg Leu Ser Arg Ser Arg
                305                 310                 315
Thr Ala Ser Leu Thr Ser Ala Ala Ser Val Asp Gly Xaa Arg Ser
            320                 325                 330
Arg Ser Arg Thr Leu Ser Gln Ser Ser Glu Ser Gly Thr Leu Phe
                335                 340                 345
Phe Gly Gly Pro Arg Gly His Thr Met Gly Leu Leu Leu Asn
            350                 355                 360
Gly Pro Cys Cys Pro Arg Val Gly Pro Ser Pro Gln Leu Xaa Gln
                365                 370                 375
Ser Asn Leu Xaa Gly Ala Glu Arg Gly His Trp Gly His Arg Lys
            380                 385                 390
Gln Arg Gly Lys Arg Ala Asp Ser Trp Arg Gly Arg
                395                 400
```

<210> SEQ ID NO 23
<211> LENGTH: 522
<212> TYPE: PRT
<213> ORGANISM: Homo sapiens
<220> FEATURE: -
<223> OTHER INFORMATION: 3688209

-continued

```
<400> SEQUENCE: 23

Met Ala Val Asn Lys Gly Leu Thr Leu Leu Asp Gly Asp Leu Pro
 1               5                  10                  15

Glu Gln Glu Asn Val Leu Gln Arg Val Leu Gln Leu Pro Val Val
                20                  25                  30

Ser Gly Thr Cys Glu Cys Phe Gln Lys Thr Tyr Thr Ser Thr Lys
                35                  40                  45

Glu Ala His Pro Leu Val Ala Ser Val Cys Asn Ala Tyr Glu Lys
                50                  55                  60

Gly Val Gln Ser Ala Ser Ser Leu Ala Ala Trp Ser Met Glu Pro
                65                  70                  75

Val Val Arg Arg Leu Ser Thr Gln Phe Thr Ala Ala Asn Glu Leu
                80                  85                  90

Ala Cys Arg Gly Leu Asp His Leu Glu Glu Lys Ile Pro Ala Leu
                95                 100                 105

Gln Tyr Pro Pro Glu Lys Ile Ala Ser Glu Leu Lys Asp Thr Ile
               110                 115                 120

Ser Thr Arg Leu Arg Ser Ala Arg Asn Ser Ile Ser Val Pro Ile
               125                 130                 135

Ala Ser Thr Ser Asp Lys Val Leu Gly Ala Ala Leu Ala Gly Cys
               140                 145                 150

Glu Leu Ala Trp Gly Val Ala Arg Asp Thr Ala Glu Phe Ala Ala
               155                 160                 165

Asn Thr Arg Ala Gly Arg Leu Ala Ser Gly Ala Asp Leu Ala
               170                 175                 180

Leu Gly Ser Ile Glu Lys Val Val Glu Tyr Leu Leu Pro Ala Asp
               185                 190                 195

Lys Glu Glu Ser Ala Pro Ala Pro Gly His Gln Gln Ala Gln Lys
               200                 205                 210

Ser Pro Lys Ala Lys Pro Ser Leu Leu Ser Arg Val Gly Ala Leu
               215                 220                 225

Thr Asn Thr Leu Ser Arg Tyr Thr Val Gln Thr Met Ala Arg Ala
               230                 235                 240

Leu Glu Gln Gly His Thr Val Ala Met Trp Ile Pro Gly Val Val
               245                 250                 255

Pro Leu Ser Ser Leu Ala Gln Trp Gly Ala Ser Val Ala Met Gln
               260                 265                 270

Ala Val Ser Arg Arg Ser Glu Val Arg Val Pro Trp Leu His
               275                 280                 285

Ser Leu Ala Ala Ala Gln Glu Glu Asp His Glu Asp Gln Thr Asp
               290                 295                 300

Thr Glu Gly Glu Asp Thr Glu Glu Glu Leu Glu Thr Glu
               305                 310                 315

Glu Asn Lys Phe Ser Glu Val Ala Ala Leu Pro Gly Pro Arg Gly
               320                 325                 330

Leu Leu Gly Gly Val Ala His Thr Leu Gln Lys Thr Leu Gln Thr
               335                 340                 345

Thr Ile Ser Ala Val Thr Trp Ala Pro Ala Ala Val Leu Gly Met
               350                 355                 360

Ala Gly Arg Val Leu His Leu Thr Pro Ala Pro Ala Val Ser Ser
               365                 370                 375

Thr Lys Gly Arg Ala Met Ser Leu Ser Asp Ala Leu Lys Gly Val
               380                 385                 390
```

-continued

```
Thr Asp Asn Val Val Asp Thr Val Val His Tyr Val Pro Leu Pro
            395             400             405

Arg Leu Ser Leu Met Glu Pro Glu Ser Glu Phe Arg Asp Ile Asp
            410             415             420

Asn Pro Pro Ala Glu Val Glu Arg Arg Glu Ala Glu Arg Arg Ala
            425             430             435

Ser Gly Ala Pro Ser Ala Gly Pro Glu Pro Ala Pro Arg Leu Ala
            440             445             450

Gln Pro Arg Arg Ser Leu Arg Ser Ala Gln Ser Pro Gly Ala Pro
            455             460             465

Pro Gly Pro Gly Leu Glu Asp Glu Val Ala Thr Pro Ala Ala Pro
            470             475             480

Arg Pro Gly Phe Pro Ala Val Pro Arg Glu Lys Pro Lys Arg Arg
            485             490             495

Val Ser Asp Ser Phe Phe Arg Pro Ser Val Met Glu Pro Ile Leu
            500             505             510

Gly Arg Thr His Tyr Ser Gln Leu Arg Lys Lys Ser
            515             520
```

DETECTION OF ALTERED EXPRESSION OF GENES REGULATING CELL PROLIFERATION

FIELD OF THE INVENTION

The present invention relates to polynucleotides comprising at least a fragment of genes that regulate cell proliferation and methods comprising the use of such polynucleotides.

BACKGROUND OF THE INVENTION

Cellular proliferation in normal tissues is strictly regulated by multiple factors and mechanisms. Cells grow and differentiate, carry out their structural or metabolic roles, participate in organismal development, and respond to their environment by altering their gene expression. Cellular functions are controlled by the timing and the amount of expression attributable to thousands of individual genes.

Aberrant cellular proliferation can be the result of under- or overexpression of genes which regulate cell growth, differentiation, and metastasis. Overexpression of oncogenes, which include growth factors, growth factor receptors, transcriptional activators, proteases, cell matrix components and other proteins necessary for cell growth regulation, can result in aberrant cell proliferation. Conversely, underexpression of regulatory proteins, inhibitors or suppressor of oncogenes, cell cycle regulators, and apoptosis inducers may contribute to abnormal cell proliferation. In many cases of aberrant cellular proliferation changes in expression of multiple factors contribute to the development of cell growth disorders such as cancers.

The present invention identifies particular polynucleotides that can be used to detect the altered expression of genes that regulate cell proliferation and consequently, diagnose diseases involving aberrant cell proliferation, such as cancer. The polynucleotides may also be used to treat such diseases.

SUMMARY OF THE INVENTION

In one aspect, the present invention provides a composition comprising one or more polynucleotides, wherein each of said polynucleotides comprises at least a fragment of a gene implicated in the regulation of cell proliferation. The plurality of polynucleotides can be selected from I) first polynucleotides, wherein each of said first polynucleotides comprises at least a fragment of a gene differentially expressed in precancerous biological samples; or II) second polynucleotides, wherein each of said second polynucleotides comprises at least a fragment of a gene differentially expressed in cancerous biological samples. The composition is useful for the detection of the altered expression of genes that regulate cell proliferation.

Generally, first polynucleotide sequences are selected by a first method comprising a) preparing more than one first, second and third transcript profiles from noncancerous, precancerous and cancerous biological samples, respectively; b) comparing said first, second and third transcript profiles to detect a plurality of genes that are differentially expressed in either noncancerous, precancerous and cancerous biological samples, respectively; and c) identifying one of said detected genes that are differentially expressed in precancerous biological samples. Second polynucleotide sequences are selected by a second method comprising a) preparing more than one first, second and third transcript profiles from noncancerous, precancerous and cancerous biological samples, respectively; b) comparing said first, second and third transcript profiles to detect a plurality of genes that are differentially expressed in either noncancerous, precancerous and cancerous biological samples, respectively; and c) identifying one of said detected genes that are differentially expressed in cancerous biological samples. The polynucleotides may be complementary DNAs (cDNAs), genomic DNA fragments, oligonucleotides and the like.

In one preferred embodiment, the composition comprises a polynucleotide comprising a sequence selected from the group consisting of: a) a polynucleotide sequence selected from the group consisting of SEQ ID NOs:1–16; b) a polynucleotide sequence, comprising a polynucleotide sequence which encodes the polypeptide sequence selected from the group consisting of: of SEQ ID NOs:17–23; c) a polynucleotide sequence having at least 70% identity to the polynucleotide sequence of (a) or (b); (d) a polynucleotide sequence comprising at least 18 sequential nucleotides of the polynucleotide sequence of (a), (b) or (c); e) a polynucleotide sequence which is complementary to the polynucleotide sequence of (a), (b),(c) or (d); and f) a polynucleotide which hybridizes under stringent conditions to the polynucleotide of (a),(b), (c), (d) or (e).

The composition is particularly useful as hybridizable array elements in a microarray for monitoring the expression of a plurality of sample polynucleotides implicated in the regulation of cell proliferation. The microarray can be used, for example, in the prognosis, diagnosis and treatment of a cancer or other disease relating to the altered expression of genes involved in cell proliferation.

In yet another aspect, the present invention provides a method for identifying polynucleotides for diagnosing, prognosing, or monitoring the progression of cancer or other diseases relating to the altered expression of genes involved in the regulation of cell proliferation. The method comprises selecting first polynucleotide sequences that comprise at least a fragment of genes differentially expressed in precancerous biological samples and second polynucleotide sequences that comprise at least a fragment of genes differentially expressed in cancerous biological samples.

Further, the present invention provides a method for diagnosing, prognosing, or monitoring the treatment of a disease. The method comprises using the composition described above comprising polynucleotide sequences to detect hybridization complexes formed between the polynucleotide sequences and sample polynucleotides. The sample polynucleotides may be from diseased, asymptomatic or nondiseased samples. The polynucleotides are contacted with a sample containing sample polynucleotides under conditions effective to form hybridization complexes between said polynucleotide sequences and sample genes that regulate cell proliferation. Hybridization complexes are then detected. The levels of hybridization complexes in diseased or nonsymptomatic samples are then compared with those in nondiseased samples.

In another aspect, the invention is a polypeptide comprising a sequence selected from the group consisting of: a) a polypeptide sequence selected from the group consisting of SEQ ID NOs:17–23; b) a polypeptide sequence having at least 70% identity to the polypeptide sequence of (a); c) a polypeptide sequence comprising at least 10 sequential amino acids of the polypeptide sequence of (a) or (b).

In another aspect, the invention entails a pharmaceutical composition comprising a polynucleotide or polypeptide in conjunction with a suitable pharmaceutical carrier and a method for treating or preventing a disease or condition associated with the altered expression of genes that regulate cell proliferation comprising administering to a subject in need such a composition in an amount effective for treating or preventing said disease.

In a further aspect, the invention provides a ribozyme that cleaves a gene whose altered expression correlates with a disease associated with cell proliferation and a method for treating or preventing a disease or condition associated with the altered expression of genes that regulate cell proliferation. The method comprises administering to a subject in need the ribozyme in an amount effective for treating or preventing said disease.

In yet another aspect, the invention provides an antisense molecule that hybridizes to a gene whose altered expression correlates with a disease associated with cell proliferation and a method for treating or preventing a disease or condition associated with the altered expression of genes that regulate cell proliferation. The method comprises administering to a subject in need the antisense molecule that hybridizes to the gene.

DESCRIPTION OF THE SEQUENCE LISTING AND TABLES

The Sequence Listing is a compilation of exemplary polynucleotide sequences obtained by sequencing clone inserts of different cDNA libraries and the amino acid sequences which are coded for by selected nucleotide sequences. Each polynucleotide sequence is identified by a sequence identification number (SEQ ID NO:), by the Incyte Clone number from which the polynucleotide sequence was first identified and by the cDNA library from which the polynucleotide sequence was obtained.

DESCRIPTION OF THE INVENTION

Definitions

A "polynucleotide sequence" refers to a chain of nucleotides. Preferably, the chain has from about 50 to 10,000 nucleotides, more preferably from about 150 to 3,500 nucleotides. In some instances, the sequences will be fully complementary (no mismatches) when aligned. In other instances, there may be up to a 30% mismatch in the sequences.

A "fragment" refers to a nucleic acid sequence that is preferably at least 10 nucleic acids in length, more preferably 40 nucleic acids, and most preferably 100 nucleic acids in length and encompasses, for example, fragments consisting of nucleic acids 1–100, 300–400, 500–600, 800–900 of SEQ ID NOs: 1–16 or fragments of similar length at the 3' end of SEQ ID NOs: 1–16. A "fragment" can also mean a stretch of at least 100 consecutive nucleotides that contains one or more deletions, insertions or substitutions. A "fragment" can also mean the whole coding sequence of a gene and may include 5' and 3' untranslated regions.

Preferred fragments are those that lack secondary structure as identified by using computer software programs such as OLIGO 4.06 Primer Analysis Software (National Biosciences), Lasergene (DNASTAR), MacDNAsis (Hitachi Software Engineering Co., Ltd.) and the like. A "fragment" can also refer to polypeptide sequences which are preferably at least 5 to about 15 amino acids in length, most preferably at least 10 amino acids long, and which retain some biological activity or immunological activity of a sequence, such as SEQ ID NOs:17–23.

The term "gene" or "genes" refers to the partial or complete coding sequence of a gene. The term also refers to 5' or 3' untranslated regions of a transcript. The phrase "gene differentially expressed in precancerous biological samples" refers to a gene whose abundance in a transcript profile derived from precancerous sample differs preferably by least about 1.5 fold, more preferably at least about 2 fold, than that in a transcript profile comprising a noncancerous sample. The phrase also refers to genes that are not detectable in the noncancerous transcript profile but are preferably at levels of at least about 2 copies per cell, more preferably at least about 3 copies per cell, in the precancerous tissue transcript profile. "Precancerous biological sample" means a sample derived from tissue adjacent a cancerous focus. Also, a precancerous sample entails the tissue condition that typically predates the appearance of cancer.

The phrase "gene differentially expressed in a cancerous biological sample" refers to a gene whose abundance in a transcript profile derived from a one or more cancerous samples differs preferably by least about 1.5 fold, more preferably at least about 2 fold, than that in a transcript profile derived from one or more noncancerous biological sample. The phrase also refers to genes that are not detectable in the noncancerous sample transcript profiles but are preferably at levels of at least about 2 copies per cell, more preferably at least about 3 copies per cell, in the cancerous sample transcript profile. "A cancerous biological sample" refers to tissue undergoing uncontrolled cell growth.

The phrase "gene differentially expressed in noncancerous biological sample" refers to a gene whose abundance in a transcript profile derived from one or more non cancerous tissues differs preferably by least about 1.5 fold, more preferably by at least about 2 fold, than that in a transcript profile comprising one or more precancerous or cancerous biological samples. The phrase also refers to genes that are not detectable in precancerous or cancerous transcript profile but are preferably at levels of at least about 2 copies per cell, more preferably at least about 3 copies per cell, in the transcript profile derived from noncancerous biological samples.

The phrase "genes that regulate cell proliferation" refers to genes whose altered expression results in a cancerous or a precancerous stage in a biological sample.

The Invention

The present invention provides polynucleotide sequences comprising at least a fragment of one or more genes that regulate cell proliferation. The polynucleotide sequences are useful individually or as a group of two or more polynucleotide sequences or fragments of a sequence selected from the group consisting of SEQ ID NOs:1–16 for diagnosis and prognosis of diseases of aberrant cell proliferation. Preferably, the plurality of polynucleotide sequences comprise at least a fragment of one or more of the polynucleotide sequences (SEQ ID NOs:1–16) presented in the Sequence Listing. In one preferred embodiment, the polynucleotide sequences comprise a plurality of polynucleotides, wherein each polynucleotide comprises at least a fragment of a sequence selected from the group consisting of SEQ ID NOs:1–16. In another embodiment, the polynucleotides comprise a plurality of polynucleotides wherein said polynucleotides comprise at least a fragment of substantially all the sequences of SEQ ID NOs:1–16. In an additional embodiment, the polynucleotide sequences comprise at least a fragment of two, five, ten, fourteen or more sequences selected from the group consisting of SEQ ID NOs:1–16.

The polynucleotide sequences are particularly useful when they are hybridizable array elements in a microarray. Such a microarray can be employed to monitor the expression of genes of unknown function, but which are differentially expressed in precancerous or cancerous tissue. In addition, the microarray can be used to monitor the expression of genes with a known function in the control of cell proliferation.

The microarray can be used for large scale genetic or gene expression analysis of a large number of polynucleotide sequences. The microarray can be used in the diagnosis of diseases, such as in the diagnosis of early stages of ductal carcinoma before other definitive symptoms are evident, and in the differential diagnosis of diseases with similar symptoms. The microarray can also be used in the monitoring and evaluation of treatments where altered expression of genes coding for polypeptides implicated in the control of cell proliferation cause disease, such as cancer. Additionally, the microarray can be used to investigate an individual's predisposition to a disease, such as cancer. Furthermore, the microarray can be employed to investigate cellular responses, such as cell proliferation and the like.

When the polynucleotide sequences of the invention are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment.

The invention also entails a pharmaceutical composition comprising a polynucleotide sequence of the invention in conjunction with a suitable pharmaceutical carrier and a method for treating or preventing a disease or condition associated with the altered expression of genes that regulate cell proliferation comprising administering to a subject in need such a composition in an amount effective for treating or preventing a disease or condition associated with cell proliferation.

The polynucleotide sequences may be selected by identifying genes that are differentially expressed in cancerous or precancerous tissue, but not in their noncancerous counterparts. Since some of the polynucleotide sequences are identified solely based on expression levels, it is not essential to know a priori the function of a particular gene in the control of cell proliferation.

Where the selection method is based on differential expression, expression sequence tag (EST) cluster analysis is employed. EST cluster analysis entails sequencing, in whole or in part, isolated clone inserts from a cDNA library, clustering overlapping sequences and determining the clustered sequences' frequency in the cDNA library. ESTs are sequenced by methods well known in the art. The methods can employ such enzymes as the Klenow fragment of DNA polymerase I, Taq polymerase, thermostable T7 polymerase, or combinations of polymerases and proofreading exonucleases. Preferably, the process is automated. ESTs can be combined to form a cluster of ESTs. Clusters are formed by identifying overlapping EST sequences and assembling the ESTs. A nucleic acid fragment assembly tool, such as the Phrap tool (WashU-Merck), the GELVIEW Fragment Assembly system (Genetics Computer Group) and the like, can be used for this purpose. The minimum number of clones necessary to constitute a cluster is two.

After assembling EST clusters, a transcript profile for a particular biological sample is generated and the frequency or abundance of a given EST cluster can be determined. The frequency of an EST cluster in a clone population is correlated to the level of expression of a particular gene. By this process those genes that are abundantly expressed in a biological sample can be identified.

Furthermore, EST analysis can be employed to identify genes that are differentially expressed in one biological sample but not in another biological sample. For this purpose, transcript profiles from both biological samples are generated and compared. By comparing transcript profiles those genes that are differentially expressed in a biological sample can be identified.

With a large enough number of transcript profiles derived from different biological samples, a statistically significant correlation can emerge between cell and tissue source information, such as disease states, treatment outcomes, exposure to various environmental factors or genotypes, and the expression levels of particular genes or groups of genes. Comparisons between transcript profiles of different cells or tissues or of the same cells or tissues under different conditions can be used to discern differences in transcriptional activities. For example, a transcript profile can show differences occurring between two different tissues, such as liver and prostate; between normal and diseased tissue, such as normal and breast tumor or between untreated and treated tissues, such as prostate tumor and irradiated prostate tumor.

The biological samples from which transcript profiles are derived can be selected from a variety of sources. For purposes of this invention, since the intent is to select polynucleotides useful for investigating gene expression as it relates to the control of cell proliferation or cancer, biological samples include those derived from noncancerous, precancerous and cancerous biological samples.

In particular, where polynucleotide sequences are sought that are derived from genes differentially expressed in precancerous tissue, the transcript profiles of precancerous tissue are compared to those of noncancerous biological samples. Examples of precancerous tissues include dysplastic bladder, breast, colon, lung and prostate tissues. Where polynucleotide sequences are sought that are derived from genes differentially expressed in cancerous tissue, the transcript profiles of cancerous tissue are compared to those of noncancerous biological samples. Examples of cancerous tissues include bladder, breast, colon, lung and prostate tumors.

Transcript profile comparisons can be obtained by methods well known to those skilled in the art. Transcript levels and profiles can be obtained and compared, for example, by a differential gene expression assay based on a quantitative hybridization of arrayed DNA clones (Nguyen, et al. (1995) *Genomics* 29: 207–216), based on the serial analysis of gene expression (SAGE) technology (Velculescu et al. (1995) *Science* 270: 484–487), based on the polymerase chain reaction (Liang et al. (1992) *Science* 257: 967–971, Prashar et al. (1996) *Proc. Natl. Acad. Sci. USA* 93: 659–663), by a differential amplification protocol (Van Gelder et al. 5,545,522)or based on electronic analysis, such as the Transcript Imaging tool or the GEMTOOLS gene expression analysis program (Incyte Pharmaceuticals) or the GeneCalling and Quantitative Expression Analysis technology (Curagen). Preferably, comparisons (subtractions) between two or more transcript profiles are performed electronically.

For purposes of this invention, a number of cDNA libraries are prepared from noncancerous, precancerous and cancerous biological samples, for example from different cDNA libraries derived from bladder, breast, colon, lung and prostate tissues which can be matched to normal and diseased conditions including precancerous and cancerous conditions. ESTs, or sequences derived from ESTs, are assembled and then analyzed to determine whether expression of the different EST clusters can be correlated in a statistical significant manner to the noncancerous, precancerous or cancerous state.

Specifically, transcript profiles can be compared to identify polynucleotide sequences whose transcripts (1) are present only in noncancerous tissue, (2) are present in noncancerous and precancerous tissue only, (3) are present in precancerous tissue only, (4) are present in precancerous and cancerous tissue only, (5) are present in cancerous tissue only, (5) are expressed at higher levels in noncancerous tissue in comparison with precancerous tissue, (6) are expressed at higher levels in noncancerous and precancerous tissue in comparison with cancerous tissue, (7) are expressed at higher levels in noncancerous and precancerous tissue in comparison with cancerous tissue, (8) are expressed at higher levels in tumor tissue in comparison with noncancerous and precancerous tissue, (9) are expressed at higher levels in precancerous tissue in comparison with noncancerous tissue, (10) are expressed at higher levels in precancerous in comparison with tumor tissue, (11) are expressed at higher levels in tumor tissue in comparison with precancerous tissue, (12) are expressed at higher levels in noncancerous in comparison with cancerous tissue, (13) are expressed at higher levels in tumor tissue in comparison with noncancerous tissue and (14) show no statistically significant differences in expression when comparing the tissues.

To identify polynucleotide sequences particularly useful in the detection of the altered expression of genes that regulate cell proliferation seven ductal carcinoma primary tumor cDNA samples and four non-diseased breast tissue cDNA samples were prepared for hybridization to diseased and non diseased sequences. Scan sensitivity, probe labeling, and cDNA quantitation controls were included in the hybridization experiments. The GEMTOOLS gene expression analysis program was used to identify gene transcripts whose expression levels in the diseased samples were at least 2-fold higher or 2-fold lower than their expression level in the non-diseased samples. These diseased sample gene transcripts were further compared in order to specifically identify those whose expression levels were consistently at least 2-fold higher or 2-fold lower in at least six of the seven diseased tissue samples than in the non-diseased samples. These specifically identified polynucleotide sequences are useful in the detection and monitoring of altered expression of genes that regulate cell proliferation. The polynucleotide sequences, SEQ ID NOs 1–16, and the amino acid sequences corresponding to some of the polynucleotide sequences, SEQ ID NOs:17–23, are provided in the Sequence Listing.

The selected polynucleotide sequences may be manipulated further to optimize the performance of the polynucleotide sequences as hybridization targets. Some sequences may not hybridize effectively under hybridization conditions due to secondary structure. To optimize polynucleotide sequence hybridization, the sequences are examined using a computer algorithm to identify fragments of genes without potential secondary structure. Such computer algorithms are well known in the art, such as OLIGO 4.06 Primer Analysis Software (National Biosciences) or Lasergene (DNASTAR, Madison Wis.). These programs can search nucleotide sequences to identify stem loop structures and tandem repeats and to analyze G+C content of the sequence (those sequences with a G+C content greater than 60% are excluded). Alternatively, the sequences can be optimized by trial and error. Experiments can be performed to determine whether sequences and complementary polynucleotide sequences hybridize optimally under experimental conditions.

Where the number of different polynucleotide sequences is desired to be greatest, the sequences are extended to assure that different polynucleotide sequences are not derived from the same gene, i.e., the polynucleotide sequences are not redundant. The sequences may be extended utilizing the partial nucleotide sequences derived from EST sequencing by employing various methods known in the art. For example, one method which may be employed, "restriction-site" PCR, uses universal primers to retrieve unknown sequence adjacent to a known locus (Sarkar, G. (1993) *PCR Methods Applic.* 2: 318–322).

The polynucleotides can be DNA or RNA, or any RNA-like or DNA-like material, such as peptide nucleic acids, branched DNAs and the like. The polynucleotide can be sense or antisense polynucleotides. In one embodiment, the polynucleotides are cDNAs. The size of the DNA sequence of interest may vary, and is preferably from 50 to 10,000 nucleotides, more preferably from 150 to 3,500 nucleotides. In a second embodiment, the polynucleotides are synthetic polynucleotides. The polynucleotides can be synthesized, in whole or in part, using chemical methods well known in the art (Caruthers et al. (1980) *Nucl. Acids Res. Symp. Ser.* 215–233).

The polynucleotides may be immobilized on a substrate. Preferred substrates are any suitable rigid or semirigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotides are bound.

In order to conduct sample analysis, a sample containing polynucleotides is provided. The samples can be any sample containing polynucleotides and obtained from any bodily fluid, cultured cells, tissue biopsies, or other tissue preparations.

DNA or RNA can be isolated from the sample according to any of a number of methods well known to those of skill in the art. For example, methods of purification of nucleic acids are described in *Laboratory Techniques in Biochemistry and Molecular Biology: Hybridization With Nucleic Acid Targets, Part I. Theory and Nucleic Acid Preparation*, P. Tijssen, ed. Elsevier (1993). When sample polynucleotides are amplified it is desirable to amplify the nucleic acid sample and maintain the relative abundances of the original sample, including low abundance transcripts. Total mRNA can be amplified by reverse transcription using a reverse transcriptase, a primer consisting of oligo d(T), and a sequence encoding the phage T7 promoter to provide a single stranded DNA template. The second DNA strand is polymerized using a DNA polymerase and a RNAse which assists in breaking up the DNA/RNA hybrid. After synthesis of the double stranded DNA, T7 RNA polymerase can be added and RNA transcribed from the second DNA strand template (Van Gelder et al. U.S. Pat. No. 5,545,522). RNA can be amplified in vitro, in situ or in vivo (See Eberwine U.S. Pat. No. 5,514,545).

The polynucleotides may be labeled with one or more labeling moieties to allow for detection of hybridized polynucleotide complexes. The labeling moieties can include compositions that can be detected by spectroscopic, photochemical, biochemical, bioelectronic, immunochemical, electrical, optical or chemical means. The labeling moieties include radioisotopes, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Hybridization causes a denatured polynucleotide and a denatured sample polynucleotide to form a stable duplex through base pairing. Hybridization methods are well known to those skilled in the art (See, for example, *Laboratory Techniques in Biochemistry and Molecular Biology*, Vol. 24: *Hybridization With Nucleic Acid Targets*, P. Tijssen, ed. Elsevier, N.Y. (1993)) Hybridization conditions can be defined by salt concentration, temperature, and other chemicals and conditions well known in the art. In particular, stringency can be increased by reducing the concentration of salt, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Stringent temperature conditions will ordinarily include temperatures of at least about 30° C., more preferably of at least about 37° C., and most preferably of at least about 60° C. Varying additional parameters, such as hybridization time, the concentration of detergent or solvent, and the inclusion or exclusion of carrier DNA, are well known to those skilled in the art. Additional variations on these conditions will be readily apparent to those skilled in the art (Wahl, G. M. and S. L. Berger (1987) Methods Enzymol. 152:399–407; Kimmel, A. R. (1987) Methods Enzymol. 152:507–511; Ausubel, F. M. et al. (1997) *Short Protocols in Molecular Biology*, John Wiley & Sons, New York, N.Y.; and Sambrook, J. et al. (1989) *Molecular Cloning A Laboratory Manual*, Cold Spring Harbor Press, Plainview, N.Y.).

Hybridization reactions can be performed in absolute or differential hybridization formats. In the absolute hybridization format, polynucleotides from one sample are hybridized to the polynucleotides in a microarray format and signals detected after hybridization complex formation correlate to polynucleotide levels in a sample. In the differential hybridization format, the differential expression of a set of genes in two biological samples is analyzed. For differential hybridization, polynucleotides from both biological samples are prepared and labeled with different labeling moieties. A mixture of the two labeled polynucleotides is added to a microarray. The microarray is then examined under conditions in which the emissions from the two different labels are individually detectable. Polynucleotides in the microarray that are hybridized to substantially equal numbers of polynucleotides derived from both biological samples give a distinct combined fluorescence (Shalon et al. PCT publication WO95/35505). In a preferred embodiment, the fluorophores Cy3 and Cy5 (Amersham Pharmacia Biotech, Piscataway N.J.) are employed as labels.

After hybridization, the microarray is washed to remove nonhybridized nucleic acids and complex formation between the hybridizable array elements and the polynucleotides is detected. Methods for detecting complex formation are well known to those skilled in the art.

In a differential hybridization experiment, polynucleotides from two or more different biological samples are labeled with two or more different fluorescent labels with different emission wavelengths. Fluorescent signals are detected separately with different photomultipliers set to detect specific wavelengths. The relative abundances/expression levels of the polynucleotides in two or more samples is obtained.

Typically, microarray fluorescence intensities can be normalized to take into account variations in hybridization intensities when more than one microarray is used under similar test conditions. In a preferred embodiment, individual polynucleotide complex hybridization intensities are normalized using the intensities derived from internal normalization controls contained on each microarray.

Diagnostic and Therapeutics

The sequences of the invention may be used in diagnosis, prognosis, treatment, prevention, and evaluation of therapies for diseases associated with cell proliferation.

In one preferred embodiment, the polynucleotides of SEQ ID NOs:1–16 or the polynucleotides encoding SEQ ID NOs:17–23 are used for diagnostic purposes to determine the absence, presence, and expression levels of genes regulating cell proliferation. The polynucleotides may be at least 10, preferably 18 nucleotides long, complementary RNA and DNA molecules, branched nucleic acids, or peptide nucleic acids (PNAs). In particular, the polynucleotides may be used to detect and quantitate gene expression in samples in which altered expression of the polynucleotides SEQ ID NOs:1–16, the polypeptides SEQ ID NOs:17–23 or the polypeptides encoded by SEQ ID NOs:1–16 are correlated with disease. Alternatively, the polynucleotides may be used to monitor the levels of such genes during therapeutic intervention. Additionally, SEQ ID NOs:1–16 can be used to detect genetic polymorphisms associated with a disease. These polymorphisms may be detected at the transcript cDNA or genomic level from mapping experiments.

The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring instances of SEQ ID NOs 1–16, sequences encoding SEQ ID NOs:17–23, allelic variants, or other related sequences.

Probes may also be used for the detection of related sequences, and should preferably have at least 70% sequence identity to any of the SEQ ID NOs:1–16.

Means for producing specific hybridization probes for DNAs encoding SEQ ID NOs:1–16 include the cloning of SEQ ID NOs:1–16 into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or 35S, or by enzymatic labels, such as alkaline phosphatase coupled to the probe via avidin/biotin coupling systems, by fluorescent labels and the like. The polynucleotide sequences may be used in Southern or northern analysis, dot blot, or other membrane-based technologies; in PCR technologies; and in microarrays utilizing fluids or tissues from patients to detect altered expression of SEQ ID NOs:1–16. Such qualitative or quantitative methods are well known in the art.

SEQ ID NOs:1–16 can be labeled by standard methods and added to a fluid or tissue sample from a patient under conditions suitable for the formation of hybridization complexes. After a suitable incubation period, the sample is washed and the signal is quantitated and compared with a standard value, typically, derived from a non-diseased sample. If the amount of signal in the patient sample is altered in comparison to the standard value then the presence of altered levels of nucleotide sequences of SEQ ID NOs:1–16 in the sample indicates the presence of the associated disease. Such assays may also be used to evaluate the efficacy of a particular therapeutic treatment regimen in animal studies, in clinical trials, or to monitor the treatment of an individual patient.

Once the presence of a disease is established and a treatment protocol is initiated, hybridization or amplification assays can be repeated on a regular basis to determine if the level of expression in the patient begins to approximate that which is observed in a healthy subject. The results obtained from successive assays may be used to show the efficacy of treatment over a period ranging from several days to months.

The polynucleotides may be used for the diagnosis of diseases associated with altered expression of genes that regulate cell proliferation such as cancer.

Alternatively, the polynucleotides may be used as targets in a microarray. The microarray can be used to monitor the expression level of large numbers of genes simultaneously and to identify splice variants, mutations, and polymorphisms. This information may be used to determine gene function, to understand the genetic basis of a disease, to diagnose a disease, and to develop and monitor the activities of therapeutic agents.

In yet another alternative, polynucleotides may be used to generate hybridization probes useful in mapping the naturally occurring genomic sequence and detecting genetic diversity. Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968). Microarrays may be used to detect genetic diversity at the genome level.

In another embodiment, antibodies which specifically bind SEQ ID NOs:17–23 may be used for the diagnosis of diseases characterized by the over-or-underexpression of SEQ ID NOs:17–23 or polypeptides encoded by SEQ ID NOs:1–16. A variety of protocols for measuring SEQ ID NOs:17–23 or the polypeptides encoded by SEQ ID NOs:1–16, including ELISAs, RIAs, and FACS, are well known in the art and provide a basis for diagnosing altered or abnormal levels of the expression of SEQ ID NOs:17–23 or the polypeptides encoded by SEQ ID NOs:1–16. Standard values for expression levels of SEQ ID NOs:17–23 are established by combining body fluids or cell extracts taken from healthy subjects, preferably human, with antibody to SEQ ID NOs:17–23 or a polypeptide encoded by SEQ ID NOs:1–16 under conditions suitable for complex formation The amount of complex formation may be quantitated by various methods, preferably by photometric means. Quantities of SEQ ID NOs:17–23 or the polypeptides encoded by SEQ ID NOs:1–16 expressed in disease samples from, for example, biopsied tissues are compared with the standard values. Deviation between standard and subject values establishes the parameters for diagnosing or monitoring disease. Alternatively, one may use competitive drug screening assays in which neutralizing antibodies capable of binding SEQ ID NOs:17–23 or the polypeptides encoded by SEQ ID NOs:1–16 specifically compete with a test compound for binding the polypeptides. Antibodies can be used to detect the presence of any peptide which shares one or more antigenic determinants with SEQ ID NOs:17–23 or the polypeptides encoded by SEQ ID NOs:1–16.

In another aspect, the polynucleotides and polypeptides of the present invention can be employed for treatment of diseases associated with the altered expression of genes associated with cell proliferation. The polynucleotides of SEQ ID NOs:1–16 or those encoding SEQ ID NOs:17–23, or any fragment or complement thereof, may be used for therapeutic purposes. In one aspect, the complement of the polynucleotides of SEQ ID NOs:1–16 or those encoding SEQ ID NOs:17–23 may be used in situations in which it would be desirable to block the transcription or translation of the mRNA, ie using antisense technologies.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides. (See, e.g., Sambrook, supra; and Ausubel, supra.) Genes having polynucleotide sequences of SEQ ID NOs:1–16 or those encoding SEQ ID NOs:17–23 can be turned off by transforming a cell or tissue with expression vectors which express high levels of a polynucleotide, or fragment thereof. Such constructs may also be used to introduce untranslatable sense or antisense sequences into a cell. Oligonucleotides derived from the transcription initiation site, e.g., between about positions –10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.)

Ribozymes, enzymatic RNA molecules, may also be used to catalyze the cleavage of mRNA and decrease the levels of particular mRNAs, such as those comprising the polynucleotide sequences of the invention. (See, e.g. Rossi, 1994, Current Biology 4: 469–471). Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Myers, (1995) Molecular Biology and Biotechnology: A Comprehensive Desk Reference, VCH Publishers, New York, N.Y.)

Alternatively, the polynucleotides of the invention may be integrated into a genome by somatic or germ cell gene therapy. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Additionally, endogeous polynucleotide expression may be inactivated using homologous recombination methods which insert inactive gene sequence at the target sequence location. (See, e.g., Thomas and Capecchi (1987) Cell 51: 503–512).

Further, an antagonist or antibody of a polypeptide of SEQ ID NOs:17–23 or a polypeptide encoded by SEQ ID NOs:1–16 may be administered to a subject to treat or prevent a cancer associated with increased expression or activity of SEQ ID NOs:17–23 or polypeptides encoded by SEQ ID NOs:1–16. An antibody which specifically binds the polypeptide may be used directly as an antagonist or indirectly as a targeting or delivery mechanism for bringing a pharmaceutical agent to cells or tissue which express the polypeptide.

Antibodies to SEQ ID NOs:17–23 or polypeptides encoded by SEQ ID NOs:1–16 may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use. Monoclonal antibodies to SEQ ID NOs:17–23 or to polypeptides encoded by SEQ ID NOs:1–16 may be prepared using any technique which provides for the production of antibody molecules by continuous cell lines in culture. These include, but are not limited to, the hybridoma technique, the human B-cell hybridoma technique, and the EBV-hybridoma technique. In addition, techniques developed for the production of chimeric antibodies can be used. (See, for example, Molecular Biology and Biotechnology, R. A. Myers, ed.,(1995)John Wiley & Sons, Inc., New York, N.Y.). Alternatively, techniques described for the production of single chain antibodies may be employed. Antibody fragments which contain specific binding sites for SEQ ID NOs:17–23 or the polypeptide sequences encoded by SEQ ID NOs:1–16 may also be generated.

Various immunoassays may be used for screening to identify antibodies having the desired specificity. Numerous protocols for competitive binding or immunoradiometric assays using either polyclonal or monoclonal antibodies with established specificities are well known in the art.

Yet further, an agonist of a polypeptide of SEQ ID NOs:17–23 or that encoded by SEQ ID NOs:1–16 may be administered to a subject to treat or prevent a cancer associated with altered expression or activity of the polypeptide.

An additional aspect of the invention relates to the administration of a pharmaceutical composition in conjunction with a pharmaceutically acceptable carrier. Such pharmaceutical compositions may consist of polynucleotides of SEQ ID Nos:1–16, polypeptides of SEQ ID NOs:17–23 or those encoded by SEQ ID NOs:1–16, antibodies to the polypeptides, and mimetics, agonists, antagonists, or inhibitors of the polypeptides. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example, polypeptides of SEQ ID NOs:17–23 or those encoded by SEQ ID NOs:1–16, or fragments thereof, antibodies of the polypeptides, and agonists, antagonists or inhibitors of the polypeptides, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics.

Any of the therapeutic methods described above may be applied to any subject in need of such therapy, including, for example, mammals such as dogs, cats, cows, horses, rabbits, monkeys, and most preferably, humans.

EXAMPLES

For purposes of example, the preparation of the BRST-NOT04 cDNA library, from which Incyte Clones 914930 and 1962202 were isolated, is described.

I cDNA Library Construction

The BRSTNOT04 cDNA library was constructed from microscopically noncancerous breast tissue removed from a 62-year-old female during unilateral extended simple mastectomy following diagnosis of invasive grade 3 (of 4), nuclear grade 2 (of 3) mammary ductal carcinoma. The surgical margins were found negative for tumor. Also, a 0.4 cm focus of in-situ carcinoma was identified in the lower quadrant of the breast. Prior to surgery, the patient was diagnosed with benign hypertension, cerebrovascular disease, atherosclerosis, hyperlipidemia, and hematuria. The patient family history included liver cancer in a sibling.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using a Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water, and DNase treated at 37° C. The RNA extraction and precipitation were repeated as before. The mRNA was then isolated with the OLIGOTEX kit (Qiagen, Chatsworth, Calif.) and used to construct the cDNA library.

The mRNA was handled according to the recommended protocols in the SuperScript Plasmid System (Life Technologies). BRSTNOT04 cDNAs were fractionated on a Sepharose CL4B column (Pharmacia Upjohn), and those cDNAs exceeding 400 bp were ligated into a pSPORT I plasmid and subsequently transformed into DH5a$^{TM}$ competent cells (Life Technologies).

The cDNA library was initiated using oligo d(T) priming. The cDNAs were treated with T4 polymerase and synthetic adapter oligonucleotides were ligated onto the cDNAs enabling them to be inserted directionally into the pINCY vector (Incyte) using Eco RI and NotI.

Plasmid DNA was released from the cells and purified using the REAL Prep 96 Plasmid Kit (Qiagen). The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

II Isolation and Sequencing of cDNA Clones

Plasmids were recovered from host cells by in vivo excision, using the UNIZAP vector system (Stratagene) or cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the REAL Prep 96 plasmid kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, F. M. (1997) *Short Protocols in Molecular Biology*, John Wiley & Sons, New York N.Y., unit 7.7).

III Homology Searching of cDNA Clones and Their Deduced Proteins

As used herein, "homology" refers to sequence similarity between a reference sequence and at least a fragment of a newly sequenced clone insert, and can refer to either a nucleic acid or amino acid sequence. The Genbank databases which contain previously identified and annotated sequences, were searched for regions of homology using BLAST (Basic Local Alignment Search Tool). (See, e.g., Altschul, S. F. (1993) *J. Mol. Evol.* 36: 290–300; and Altschul et al. (1990) *J. Mol. Biol.* 215: 403–410.)

BLAST involves first finding similar segments between the query sequence and a database sequence, then evaluating the statistical significance of any matches that are found and finally reporting only those matches that satisfy a user-selectable threshold of significance. BLAST produces alignments of both nucleotide and amino acid sequences to determine sequence similarity. The fundamental unit of the BLAST algorithm output is the High scoring Segment Pair (HSP). An HSP consists of two sequence fragments of arbitrary, but equal lengths, whose alignment is locally maximal and for which the alignment score meets or exceeds a threshold or cutoff score set by the user.

The basis of the search is the product score, which is defined as:

$$\frac{\% \text{ sequence identity} \times \% \text{ maximum } BLAST \text{ score}}{100}$$

The product score takes into account both the degree of similarity (identity) between two sequences and the length of the sequence match as reflected in the BLAST score. The BLAST score is calculated by scoring +5 for every base that matches in an HSP and −4 for every mismatch. For example, with a product score of 40, the match will be exact within a 1% to 2% error, and, with a product score of 70, the match will be exact. Homologous molecules are usually identified by selecting those which show product scores between 15 and 40, although lower scores may identify related molecules. The P-value for any given HSP is a function of its expected frequency of occurrence and the number of HSPs observed against the same database sequence with scores at least as high. Percent sequence identity refers to the percentage of sequence similarity found in a comparison of two or more amino acid or nucleic acid sequences. Percent identity can be determined electronically, e.g., by using the MegAlign program (DNASTAR, Inc., Madison Wis.). The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity.

IV Transcript Imaging

To discover transcripts that were differentially expressed in noncancerous, precancerous and cancerous biological samples, the following cDNA libraries were employed: cDNA libraries derived from noncancerous bladder (BLADNOT01, BLADNOT04), precancerous bladder (BLADNOT03, BLADNOT05, BLADNOT06), cancerous bladder (BLADTUT02, BLADTUT04, BLADTUT05, BLADTUT06, BLADTUT07); noncancerous breast (BRSTNOM01, BRSTNOM02, BRSTNOT01, BRSTNOT02), precancerous breast (BRSTNOT03, BRSTNOT04, BRSTNOT05, BRSTNOT07, BRSTNOT09, BRSTNOT13, BRSTNOT14),cancerous breast (BRSTTUT01, BRSTTUT02, BRSTTUT03, BRSTTUT08, BRSTTUT13); noncancerous colon (COLNNOT13, COLNOT19), precancerous colon (COLNNOT01, COLNNOT05, COLNNOT07, COLNNOT08, COLNNOT09, COLNNOT11, COLNNOT16), cancerous colon (COLNTUM01, COLNTUT02, COLNTUT03, COLNTUT06, COLNTUT15, COLNTUT16, COLNPOT01); noncancerous lung (LUNGNOM01, LUNGNOT001, LUNGNOT02, LUNGNOT04), precancerous lung (LUNGNOT03, LUNGNOT04, LUNGNOT12, LUNGNOT14, LUNGNOT15, LUNGNOT18), cancerous lung (LUNGTUM01, LUNGTUT01, LUNGTUT03, LUNGTUT06, LUNGTUT07, LUNGTUT08, LUNGTUT09, LUNGTUT10, LUNGTUT11); noncancerous prostate (PROSNOT01, PROSNOT11, PROSNON01), precancerous prostate (PROSNOT02, PROSNOT05, PROSNOT06, PROSNOT07, PROSNOT14, PROSNOT15, PROSNOT16, PROSNOT18, PROSNOT19, PROSNOT20, PROSNOT26, PROSNON08), cancerous prostates (PROSTUT01, PROSTUT03, PROSTUT04, PROSTUT05, PROSTUT08, PROSTUT09, PROSTUT10, and PROSTUT12).

Transcript expression was analyzed by using a program that (a) assembled the sequences into clusters and (b)

classified the sequences according to where the sequences were expressed. Also, the statistical significance of the expression patterns was analyzed. The categories were as follows: (1) are present only in noncancerous tissue, (2) are present in noncancerous and precancerous tissue only, (3) are present in precancerous tissue only, (4) are present in precancerous and tumor tissue only, (5) are present in tumor only, (5) are expressed at higher levels in noncancerous tissue in comparison with precancerous tissue, (6) are expressed at higher levels in noncancerous and precancerous tissue in comparison with cancerous tissue, (7) are expressed at higher levels in noncancerous and precancerous tissue in comparison with cancerous tissue, (8) are expressed at higher levels in cancerous tissue in comparison with non-cancerous and precancerous tissue, (9) are expressed at higher levels in precancerous rather in comparison with noncancerous tissue, (10) are expressed at higher levels in precancerous in comparison with cancerous tissue, (11) are expressed at higher levels in cancerous tissue in comparison with precancerous tissue, (12) are expressed at higher levels in noncancerous tissue rather than in cancerous tissue, (13) are expressed at higher levels in tumor tissue rather than in noncancerous tissue and (14) no statistically significant differences in expression. For categories (1) through (5), the statistically significant cutoff point was selected whereby the transcript should be expressed in at least 50% of the libraries, if the number of libraries was equal or greater than 4 but less than 10. If the number of libraries was greater than 10, then the transcript only needed to be expressed in 33% of the libraries. When fewer than 4 libraries were available, a transcript would typically have to be expressed in all tissue samples for selection. For categories (6) through (13), selected transcripts were expressed at levels greater than 2.5×, more preferably at levels of about 3× and 4× in the tissue where overexpression is observed. Also at least 50% of the cDNA libraries of a given biological sample type have to show overexpression.

V Sample Preparation

PolyA$^+$ RNA was purchased from BioChain Institute (San Leandro, Calif., USA) where total RNA was isolated from tissue samples using the guanidinium thiocyanate method and poly$^+$ RNA was purified using the oligo (dT)cellulose method. The four non-diseased breast tissue polyA$^+$ RNA samples were prepared from tissue from three female patients, ages 32–42 and a pooled tissue sample from two donors, ages 43 and 58. The seven ductal carcinoma primary tumor tissue polyA$^+$ RNA samples were prepared from tissue from six different female patients, ages 46–56 and a pool of 18 donors (ages 40–72), all undergoing no chemotherapeutic treatment. Each polyA$^+$ RNA sample was reverse transcribed using MMLV reverse-transcriptase, 0.05 pg/ul oligo-dT primer (21mer), 1×first strand buffer, 0.03 units/ul RNase inhibitor, 500 uM dATP, 500 uM dGTP, 500 uM dTTP, 40 uM dCTP, 40 uM dCTP-Cy3 (BDS) or dCTP-Cy5 (Amersham Pharmacia Biotech). The reverse transcription reaction was performed in a 25 ml volume containing 200 ng polyA$^+$ RNA with GEMBRIGHT kits (Incyte). Specific control polyA$^+$ RNAs (YCFR06, YCFR45, YCFR67, YCFR85, YCFR43, YCFR22, YCFR23, YCFR25, YCFR44, YCFR26) were synthesized by in vitro transcription from non-coding yeast genomic DNA (W. Lei, unpublished). As quantitative controls, the control mRNAs (YCFR06, YCFR45, YCFR67, YCFR85) at 0.002 ng, 0.02 ng, 0.2 ng, and 2 ng were diluted into reverse transcription reaction at ratios of 1:100,000, 1:10,000, 1:1000, 1:100 (w/w) to sample mRNA respectively. The control mRNAs (YCFR43, YCFR22, YCFR23, YCFR25, YCFR44, YCFR26) were diluted into reverse transcription reaction at ratios of 1:3, 3:1, 1:10, 10:1, 1:25, 25:1 (w/w) to sample mRNA differential expression patterns. After incubation at 37° C. for 2 hr, each reaction sample (one with Cy3 and another with Cy5 labeling) was treated with 2.5 m 1 of 0.5M sodium hydroxide and incubated for 20 minutes at 85° C. to the stop the reaction and degrade the RNA. Probes were purified using two successive CHROMA SPIN 30 gel filtration spin columns (Clontech, Palo Alto, Calif. USA) and after combining, both reaction samples were ethanol precipitated using 1 ml of glycogen (1 mg/ml), 60 ml sodium acetate, and 300 ml of 100% ethanol. The probe was then dried to completion using a SpeedVAC (Savant) and resuspended in 14 ul 5×SSC/0.2% SDS.

VI Microarray Preparation

Purified array elements were immobilized on polymer-coated glass slides. Glass microscope slides (Corning, Coming, N.Y.) cleaned by ultrasound in 0.1% SDS and acetone, with extensive distilled water washes between and after treatments. Glass slides were etched in 4% hydrofluoric acid (VWR, West Chester, Pa.), washed extensively in distilled water, and coated with 0.05% aminopropyl silane (Sigma Aldrich, St. Louis, Mo.) in 95% ethanol. Coated slides were cured in a 110° C. oven.

Array elements were applied to the coated glass substrate using a procedure described in U.S. Pat. No. 5,807,522 and incorporated herein by reference. In brief, 1 $\mu$l of the array element DNA, at an average concentration of 100 ng/ul, was loaded into the open capillary printing element by a high-speed robotic apparatus. The apparatus then deposited about 5 nl of array element sample per slide.

Microarrays were UV-crosslinked using a STRATALINKER UV-crosslinker (Stratagene, La Jolla, Calif.). Microarrays were washed at room temperature once in 0.2% SDS and three times in distilled water. Non-specific binding sites were blocked by incubation of microarrays in 0.2% casein in phosphate buffered saline (PBS) (Tropix Inc., Bedford, Mass.) for 30 minutes at 60° C. followed by washes in 0.2% SDS and distilled water as before.

VII Hybridization

Hybridization reactions contained 9 $\mu$l of probe mixture consisting of 0.2 $\mu$g each of both Cy3 and Cy5 labeled cDNA synthesis products in 5×SSC, 0.2% SDS hybridization buffer. The probe mixture was heated to 65° C. for 5 minutes and was aliquoted onto the microarray surface and covered with an 1.8 cm$^2$ coverslip. The arrays were transferred to a waterproof chamber having a cavity just slightly larger than a microscope slide. The chamber was kept at 100% humidity internally by the addition of 140 $\mu$of 5×SSC in a corner of the chamber. The chamber containing the arrays was incubated for about 6.5 hours at 60° C. The arrays were washed for 10 min at 45° C. in high stringency wash buffer (1×SSC, 0.1% SDS), three times for 10 minutes each at 45° C. in low stringency wash buffer (0.1×SSC), and then dried.

VIII Detection

The microscope used to detect the reporter-labeled hybridization complexes was equipped with an Innova 70 mixed gas 10 W laser (Coherent Lasers, Santa Clara, Calif.) capable of generating spectral lines at 488 nm for excitation of Cy3, and 632 nm for excitation of Cy5. The excitation laser light was focused on the array using a 20×microscope objective (Nikon). The slide containing the array was placed on a computer-controlled X-Y stage on the microscope and raster-scanned past the objective. The 1.8 cm×1.8 cm array used in the present example was scanned with a resolution of 20 micrometers.

In two separate scans, a mixed gas multiline laser excited the two fluorophores sequentially. Emitted light was split, based on wavelength, into two photomultiplier tube detectors (PMT R1477, Hamamatsu Photonics, San Jose, Calif.) corresponding to the two fluorophores. Appropriate filters positioned between the array and the photomultiplier tubes were used to filter the signals. The emission maxima of the fluorophores used were 565 nm for Cy3 and 650 nm for Cy5. Each array was typically scanned twice, one scan per fluorophore using the appropriate filters at the laser source, although the apparatus was capable of recording the spectra from both fluorophores simultaneously.

The sensitivity of the scans was typically calibrated using the signal intensity generated by a cDNA control species added to the probe mix at a known concentration. A specific location on the array contained a complementary DNA sequence, allowing the intensity of the signal at that location to be correlated with a weight ratio of hybridizing species of 1:100,000. When two probes from different sources (e.g., representing test and control cells), each labeled with a different fluorophore, are hybridized to a single array for the purpose of identifying genes that are differentially expressed, the calibration was done by labeling samples of the calibrating cDNA with the two fluorophores and adding identical amounts of each to the hybridization mixture.

The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte).

IX Results

The GEMTOOLS (Incyte) gene expression analysis program was used to identify gene transcripts whose expression levels in the diseased samples was at least 2-fold higher or 2-fold lower than their expression level in the non-diseased samples. These diseased sample gene transcripts were further compared in order to specifically identify those whose expression levels were consistently at least 2-fold higher or 2-fold lower in six of the seven diseased tissue samples than in the non-diseased samples. These specifically identified gene transcripts are useful in the detection and monitoring of altered expression of genes that regulate cell proliferation. The polynucleotide sequences, SEQ ID NOs 1–16, and the amino acid sequences, SEQ ID NOs 17–23, are provided in the Sequence Listing. Table 1 is a list of the exemplary polynucleotide sequences according to their SEQ ID NOs. Column 1 shows the sequence identification numbers (SEQ ID NO:), column 2 lists the Incyte Clone ID numbers, and column 3, the cDNA libraries from which these clones were isolated. The fourth column describes a relevant Genbank identification number match, if any. The fifth column contains the annotation associated with the referenced GenBank identification number. For polynucleotide sequences that are not exact matches or homologous to GenBank nucleotide sequences the fourth and fifth columns contain the words INCYTE.

TABLE 1

| Nucleotide SEQ ID NO: | Clone ID | Library | Genbank Identifier | Annotation |
|---|---|---|---|---|
| 1 | 159452 | ADENINB01 | g163430 | osteoinductive factor |
| 2 | 914930 | BRSTNOT04 | INCYTE | INCYTE |
| 3 | 1283330 | COLNNOT16 | INCYTE | INCYTE |
| 4 | 1299627 | BRSTNOT07 | INCYTE | INCYTE |
| 5 | 1319129 | BLADNOT04 | INCYTE | INCYTE |
| 6 | 1698542 | BLADTUT05 | INCYTE | INCYTE |
| 7 | 1962202 | BRSTNOT04 | INCYTE | INCYTE |
| 8 | 2083433 | UTRSNOT08 | INCYTE | INCYTE |
| 9 | 2227688 | SEMVNOT01 | g3046386 | Nickel inducible gene |
| 10 | 2313925 | NGANNOT01 | INCYTE | INCYTE |
| 11 | 2507107 | CONUTUT01 | INCYTE | INCYTE |
| 12 | 2544503 | UTRSNOT11 | INCYTE | INCYTE |
| 13 | 3044710 | HEAANOT01 | INCYTE | INCYTE |
| 14 | 3507515 | CONCNOT01 | INCYTE | INCYTE |
| 15 | 3540909 | SEMVNOT04 | g2661034 | Homo sapiens mRNA sequence |
| 16 | 3688209 | HEAANOT01 | g457374 | perilipin A |

SEQ ID NO: 17 corresponds to a translation of polynucleotide sequence SEQ ID NO:1. SEQ ID NO: 18 corresponds to a translation of polynucleotide sequence SEQ ID NO:4. SEQ ID NO: 19 corresponds to a translation of polynucleotide sequence SEQ ID NO:9. SEQ ID NO: 20 corresponds to a translation of polynucleotide sequence SEQ ID NO:11. SEQ ID NO: 21 corresponds to a translation of polynucleotide sequence SEQ ID NO:13. SEQ ID NO: 22 corresponds to a translation of polynucleotide sequence SEQ ID NO:14. SEQ ID NO: 23 corresponds to a translation of polynucleotide sequence SEQ ID NO:16.

What is claimed is:

1. A composition comprising a plurality of cDNAs for use in detecting the altered expression of genes in a cancerous or precancerous biological sample, wherein each of the cDNAs comprises a sequence selected from the group consisting of:

a) SEQ ID NOs:1–16, b) a cDNA encoding a polypeptide selected from the group consisting of SEQ ID NOs:18–23, and c) a cDNA sequence which is completely complementary to the cDNA sequence of (a) or (b).

2. The composition of claim 1, wherein said cDNAs are immobilized on a substrate.

3. The composition of claim 1, wherein said biological samples are selected from the group consisting of bladder, breast, colon, lung and prostate samples.

4. A cDNA comprising a sequence selected from the group consisting of:

a) SEQ ID NOs:1–16;

b) a cDNA sequence which encodes a polypeptide sequence selected from the group consisting of SEQ ID NOs:18–22; and c) a cDNA sequence which is completely complementary to the cDNA sequence of (a) or (b).

5. A method for diagnosing or monitoring the treatment of a cancerous or precancerous condition in a sample, said method comprising:

a) obtaining nucleic acids from a sample;

b) contacting the nucleic acids of the sample with an array comprising a plurality of cDNAs of claim 1 under conditions to form one or more hybridization complexes;

c) detecting said hybridization complexes; and d) comparing the levels of the hybridization complexes detected in step (c) with the level of hybridization complexes detected in a non-diseased sample, wherein the altered level of hybridization complexes detected in step (c) compared with the level of hybridization complexes of a non-diseased sample correlates with the presence of a cancerous or precancerous condition.

6. The method of claim 5, wherein said cDNAs are immobilized on a substrate.

7. The method of claim 5, wherein said biological samples are selected from the group consisting of bladder, breast, colon, lung and prostate samples.

8. A method for detecting a polynucleotide in a sample, the method comprising the steps of:

(a) hybridizing the cDNA of claim 4 to at least one nucleic acid of the sample to form a hybridization complex; and (b) detecting the hybridization complex, wherein the presence of the hybridization complex correlates with the presence of the polynucleotide in the sample.

9. A composition comprising the cDNA of claim 4 in conjunction with a suitable carrier.

* * * * *